(12) United States Patent
Arai et al.

(10) Patent No.: US 10,631,832 B2
(45) Date of Patent: Apr. 28, 2020

(54) ULTRASONIC MODULE, ULTRASONIC APPARATUS, AND METHOD OF CONTROLLING ULTRASONIC MODULE

(71) Applicant: SEIKO EPSON CORPORATION, Tokyo (JP)

(72) Inventors: Yoshio Arai, Shiojiri (JP); Kenji Murakami, Shiojiri (JP)

(73) Assignee: SEIKO EPSON CORPORATION, Tokyo (JP)

( * ) Notice: Subject to any disclaimer, the term of this patent is extended or adjusted under 35 U.S.C. 154(b) by 627 days.

(21) Appl. No.: 15/253,082

(22) Filed: Aug. 31, 2016

(65) Prior Publication Data
US 2017/0065260 A1    Mar. 9, 2017

(30) Foreign Application Priority Data

Sep. 9, 2015 (JP) ................. 2015-177319

(51) Int. Cl.
  *A61B 8/00* (2006.01)
  *G01S 7/52* (2006.01)
  *A61B 8/08* (2006.01)

(52) U.S. Cl.
  CPC .............. *A61B 8/56* (2013.01); *A61B 8/5207* (2013.01); *A61B 8/54* (2013.01); *G01S 7/5208* (2013.01); *G01S 7/52077* (2013.01); *G01S 7/52096* (2013.01); *A61B 8/4494* (2013.01)

(58) Field of Classification Search
  CPC .............. G01S 7/52077; G01S 7/52082; G01S 7/52085; G01S 7/52087; G01S 7/52096; G01S 7/5208; A61B 8/5207; A61B 8/5215; A61B 8/5269; A61B 8/54; A61B 8/4494; A61B 8/56; H02J 1/02; H02M 1/14
  See application file for complete search history.

(56) References Cited

U.S. PATENT DOCUMENTS

2014/0066778 A1 * 3/2014 Nishiwaki ............. B06B 1/0215
                                                    600/459

FOREIGN PATENT DOCUMENTS

| JP | H05-300889 A | 11/1993 |
| JP | H10-201732 A | 8/1998 |
| JP | 2012-065694 A | 4/2012 |
| JP | 5481334 | * 4/2014 |
| JP | 2014-083155 A | 5/2014 |
| JP | 2014-083155 | * 12/2014 |

* cited by examiner

*Primary Examiner* — Bo Joseph Peng
(74) *Attorney, Agent, or Firm* — Oliff PLC

(57) ABSTRACT

An ultrasonic module includes a reception circuit adapted to receive a reception signal from an ultrasonic device, which receives an ultrasonic wave, to generate an echo signal, switching power supplies driven with a predetermined switching cycle, and adapted to supply the reception circuit with electrical power, and a phasing addition circuit adapted to perform an addition process on a first echo signal output when driving the reception circuit at a first drive timing in the switching cycle, and a second echo signal output when driving the reception circuit at a second drive timing delayed as much as a half cycle of a switching noise in the switching power supplies from the first drive timing.

9 Claims, 11 Drawing Sheets

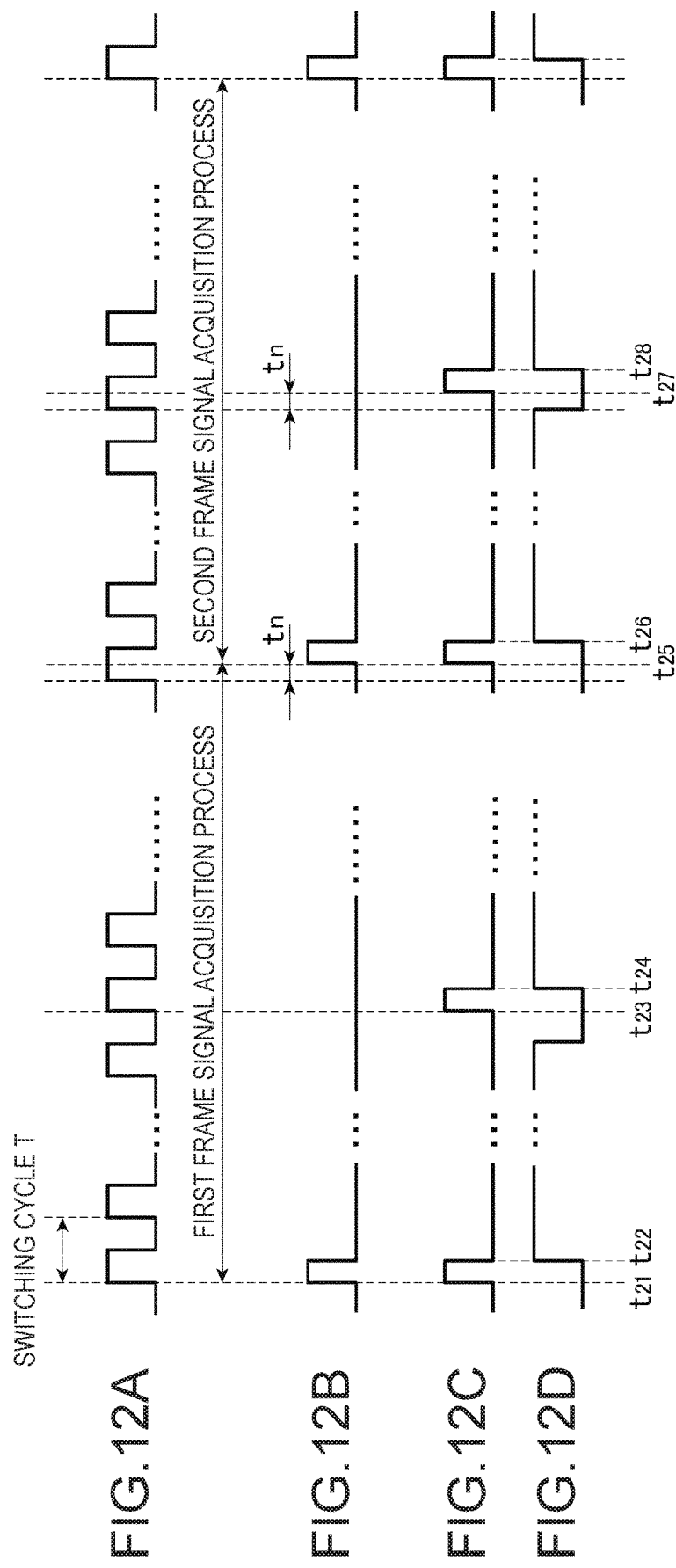

ULTRASONIC MODULE, ULTRASONIC APPARATUS, AND METHOD OF CONTROLLING ULTRASONIC MODULE

BACKGROUND

1. Technical Field

The present invention relates to an ultrasonic module, an ultrasonic apparatus, and a method of controlling the ultrasonic module.

2. Related Art

In the past, there has been known an ultrasonic apparatus for generating an internal tomographic image of an object such as a living body by receiving the ultrasonic wave reflected by the inside of the object. In such an ultrasonic apparatus, in recent years, in order to miniaturize the device, there is used a switching power supply as a power supply for supplying a receiving circuit of the ultrasonic wave with electrical power.

However, since the switching power supply performs switching at a high rate with semiconductor elements, high frequency noise (switching noise) easily occurs. If the switching noise is mixed in when processing a signal, which has been received in the ultrasonic element, with the receiving circuit, artifacts occur in the image.

To cope with the above, there has been proposed a configuration of suppressing an influence of the switching noise of the switching power supply (see, e.g., JP-A-2012-65694 (Document 1) and JP-A-2014-83155 (Document 2)).

In the ultrasonic apparatus described in Document 1, transmission and reception of the ultrasonic wave are performed while shifting the timing of each of the transmission and the reception of the ultrasonic wave for obtaining a plurality of echo signals obtained from the same scan line with respect to the switching timing (phase) of the switching power supply. Thus, in the case of performing a phasing addition process on each of the signals, the switching noise is prevented from overlapping each other in the same phase to suppress an increase in the artifacts to the internal tomographic image (B mode image).

Further, in the ultrasonic apparatus described in Document 2, an increase in the artifacts is suppressed by making the plurality of switching power supplies operate with respective switching cycles different from each other to thereby disperse the switching noise.

Incidentally, in the related art configuration described in Document 1 and Document 2 described above, although the artifacts are decreased by dispersing the switching noise, the switching noise itself does not decrease. Therefore, granular artifacts remain partially in some cases, and there is a problem that the artifacts cannot sufficiently be decreased and the measurement result high in accuracy cannot be obtained.

SUMMARY

An advantages of some aspects of the invention is to provide an ultrasonic module, an ultrasonic apparatus, and a method of controlling the ultrasonic module each capable of obtaining a highly accurate ultrasonic measurement result.

An ultrasonic module according to an application example of the invention includes a reception circuit section adapted to receive a signal from an ultrasonic device, which receives an ultrasonic wave, to generate a processed signal, a switching power supply driven with a predetermined switching cycle, and adapted to supply the reception circuit section with electrical power, and a signal addition section adapted to perform an addition process on a first processed signal output when driving the reception circuit section at a first drive timing in the switching cycle, and a second processed signal output when driving the reception circuit section at a second drive timing delayed as much as a half cycle of a switching noise in the switching power supply from the first drive timing.

In this application example, the addition process is performed on the first processed signal output from the reception circuit section when driving the reception circuit section at the first drive timing in the switching cycle of the switching power supply, and the second processed signal output from the reception circuit section when driving the reception circuit section at the second drive timing in the switching cycle. Here, the second drive timing is a timing shifted as much as a half cycle of the switching noise from the first drive timing. Therefore, the switching noise to be superimposed on the first processed signal and the switching noise to be superimposed on the second processed signal are shifted as much as a half cycle from each other. Therefore, when the addition process is performed on the first processed signal and the second processed signal, the switching noises are cancelled out with each other, and thus the switching noises can be reduced. Therefore, since the switching noise itself can be reduced, the ultrasonic measurement result high in accuracy can be obtained compared to the related art configuration of dispersing the switching noise.

In the ultrasonic module according to the application example, it is preferable that the second drive timing is a timing delayed as much as a half cycle with respect to a cycle of a switching $N^{th}$-order harmonic wave of the switching power supply.

In this application example, the second drive timing is set to the timing delayed as much as a half cycle with respect to the cycle of the switching $N^{th}$-order harmonic wave of the switching power supply (with respect to the $N^{th}$-order switching noise). The first-order switching noise through the Nth-order switching noise are generated from the switching power supply, and the lower-ordered switching noises are out of the band, and can therefore easily be removed by, for example, a high-pass filter. In contrast, the $N^{th}$-order switching noise cannot be removed by the high-pass filter, and remains superimposed in the first processed signal and the second processed signal. Here, in this application example, since the second drive timing is delayed as much as a half cycle of such an Nth-order switching noise, the Nth-order switching noise to be superimposed on the first processed signal and the Nth-order switching noise to be superimposed on the second processed signal can be cancelled out with each other.

In the ultrasonic module according to the application example, it is preferable that the ultrasonic device includes a first ultrasonic reception section, and a second ultrasonic reception section different from the first ultrasonic reception section, the reception circuit section includes a first reception circuit adapted to receive a signal from the first ultrasonic reception section and output the first processed signal, and a second reception circuit adapted to receive a signal from the second ultrasonic reception section and output the second processed signal, and the switching power supply includes a first switching power supply adapted to supply the first reception circuit with electrical power with the switching cycle from the first drive timing, and a second switching power supply adapted to supply the second reception circuit with electrical power with the switching cycle from the second drive timing.

In this application example, the reception circuit section includes the first reception circuit and the second reception circuit, the reception signal from the first ultrasonic reception section provided to the ultrasonic device is input to the first reception circuit, and the reception signal from the second ultrasonic reception section of the ultrasonic device is input to the second reception circuit. Further, the first reception circuit is driven by the first switching power supply, and the second reception circuit is driven by the second switching power supply. Here, the second switching power supply drives the second reception circuit at the second drive timing delayed as much as a half cycle of the switching noise from the first drive timing at which the first switching power supply drives the first reception circuit. In other words, a shift corresponding to a half cycle of the switching noise occurs between the switching cycle of the first switching power supply and the switching cycle of the second switching power supply.

Therefore, similarly to the application example described above, the switching noise to be superimposed on the second processed signal is also shifted as much as a half cycle of the switching noise with respect to the switching noise to be superimposed on the first processed signal, and by performing the addition process on these signals, the switching noise can be reduced.

Further, in this application example, by controlling the drive timings of the first switching power supply and the second switching poser supply, reduction of the switching noise can easily be achieved, and thus, the configuration such as a filter for removing the noise can be simplified. Therefore, simplification of the configuration of the ultrasonic module can be achieved.

In the ultrasonic module according to the application example, it is preferable that the ultrasonic device includes a plurality of ultrasonic element groups arranged along one direction, the first ultrasonic reception section is constituted by the ultrasonic element groups located at odd-numbered positions along the one direction, and the second ultrasonic reception section is constituted by the ultrasonic element groups located at even-numbered positions along the one direction.

In general, in the case of receiving the ultrasonic wave reflected by the object with a plurality of ultrasonic element groups, the reception signals of the ultrasonic element groups adjacent to each other become to have respective waveforms similar to each other. On the other hand, the longer the distance between the ultrasonic element groups is, the longer the delay in the transmission of the ultrasonic wave becomes, and thus the reception timing of the ultrasonic wave is delayed to cause a difference in the signal waveform. Here, in the case of performing the addition process to the processed signals of the ultrasonic wave, the phase shift is performed taking the time until the reception timing of each of the ultrasonic element groups into consideration as the delay time, and then, the signal addition is performed. Therefore, as described above, in the case of adding the processed signals from the distant ultrasonic element groups, the phase shift amount based on the delay time becomes large, the position of the switching noise is also shifted. Even in this case, since it results that the switching noise is dispersed, there is no chance for the artifacts to appear markedly. However, since the switching shift cannot sufficiently be reduced, it results that the noise component remains, and thus sufficient increase in accuracy is not achieved.

In contrast, in this application example, the ultrasonic device has a plurality of ultrasonic element groups arranged in one direction, and the odd-numbered ultrasonic element groups are connected to the first reception circuit, and the even-numbered ultrasonic element groups are connected to the second reception circuit out of the plurality of ultrasonic element groups. Therefore, by adding the first processed signal based on the reception signal from the odd-numbered ultrasonic element groups and the second processed signal based on the reception signal from the even-numbered ultrasonic element groups to each other, it results that the signals similar to each other are added to each other. Thus, the switching noise can effectively be reduced, and thus, the measurement accuracy of the ultrasonic measurement can be improved.

In the ultrasonic module according to the application example, it is preferable that the ultrasonic device includes a plurality of ultrasonic element groups arranged along one direction, the first ultrasonic reception section is constituted by the ultrasonic element groups disposed on one side of a central position in the one direction out of the plurality of ultrasonic element groups along the one direction, and the second ultrasonic reception section is constituted by the ultrasonic element groups disposed on the other side of the central position in the one direction out of the plurality of ultrasonic element groups along the one direction.

In this application example, out of the plurality of ultrasonic element groups arrange in the one direction, the ultrasonic element groups located on one side from the central position in the one direction are connected to the first reception circuit, and the ultrasonic element groups located on the other side are connected to the second reception circuit. In such a configuration, simplification of the connection wiring between the ultrasonic device and each of the reception circuit sections can be achieved.

In the ultrasonic module according to the application example, it is preferable that a clock control section adapted to control drive timings of the first switching power supply and the second switching power supply is further included.

Normally, the switching cycle of the switching power supply is output from the clock incorporated in the switching power supply. In contrast, in this application example, as described above, it is necessary to drive the first switching power supply and the second switching power supply while being shifted as much as a half cycle of the switching noise from each other. In the case of performing the control based on the clock incorporated in each of the switching power supplies, there is required the constituent such as a clock control circuit for outputting the clock signal (clock cycle) of the first switching power supply to the second switching power supply, and synchronizing the switching cycles in the second switching power supply at a timing shifted as much as a half cycle from the clock cycle thus input. In contrast, in this application example, the drive timings of the first switching power supply and the second switching power supply are controlled using the clock control section provided separately. In such a configuration, it is sufficient to command the drive timings to the first switching power supply and the second switching power supply, and the simplification of the configuration and the process can be achieved.

In the ultrasonic module according to the application example, it is preferable that an ultrasonic control section adapted to perform a transmission process and a reception process of an ultrasonic wave by the ultrasonic device in sync with each other is further included, wherein the ultrasonic device includes an ultrasonic transmission section adapted to transmit the ultrasonic wave, and the ultrasonic control section makes the ultrasonic device perform the transmission process and the reception process in sync with each other at the first drive timing to make the reception circuit section output the first processed signal, and makes the ultrasonic device perform the transmission process and the reception process in sync with each other at the second drive timing to make the reception circuit section output the second processed signal.

In this application example, the addition process is performed on the first processed signal obtained when performing the transmission/reception process of the ultrasonic wave at the first drive timing in the switching cycle of the switching power supply, and the second processed signal obtained when performing the transmission/reception process at the second drive timing in the switching cycle.

For example, the transmission/reception process of the ultrasonic wave is performed at the first drive timing in the switching cycle to obtain the first processed signal corresponding to one frame from the reception circuit section. Subsequently, the transmission/reception process of the ultrasonic wave is performed at the second drive timing delayed as much as a half cycle of the switching noise from the first drive timing in the switching cycle to obtain the second processed signal corresponding to one frame from the reception circuit section. Then, the first processed signal and the second processed signal are added to each other. In such a case, it results that the processed signal for forming one frame of image is obtained in a period of time in which the processed signal corresponding to two frames can be received. However, similarly to the application example described above, by performing the addition process on the processed signals, the switching noise can be reduced and the measurement result high in accuracy can be obtained, and it becomes possible to, for example, form the highly accurate image based on these processed signals.

Further, since the plurality of switching power supplies and the plurality of reception circuit sections becomes unnecessary, simplification of the configuration can be achieved, and miniaturization of the ultrasonic module can be achieved.

An ultrasonic apparatus according to an application example of the invention includes a reception circuit section adapted to receive a signal from an ultrasonic device, which receives an ultrasonic wave, to generate a processed signal, a switching power supply driven with a predetermined switching cycle, and adapted to supply the reception circuit section with electrical power, a signal addition section adapted to perform an addition process on a first processed signal output when driving the reception circuit section at a first drive timing, and a second processed signal output when driving the reception circuit section at a second drive timing delayed as much as a half cycle of a switching noise in the switching power supply from the first drive timing, and an image processing section adapted to generate an internal tomographic image of an object based on a signal obtained by the addition process of the signal addition section.

In this application example, there are provided the ultrasonic module according to the application example described above, and the image processing section adapted to form an image based on the signal (addition signal) obtained by performing the addition process on the first processed signal and the second processed signal in the signal addition section of the ultrasonic module.

As described above, in the ultrasonic module, even in the case in which the switching noise of the switching power supply is superimposed on the processed signals, these switching noises can be reduced. Therefore, by forming the image based on the addition signal with the switching noise reduced, it is possible to form the highly accurate image while preventing the artifacts from occurring.

A method of controlling an ultrasonic module according to an application example of the invention is a method of controlling an ultrasonic module including a reception circuit section adapted to receive a signal from an ultrasonic device, which receives an ultrasonic wave, to generate a processed signal and a switching power supply driven with a predetermined switching cycle, and adapted to supply the reception circuit section with electrical power, the method including the steps of outputting a first processed signal from the reception circuit section by driving the reception circuit section at a first drive timing in the switching cycle, outputting a second processed signal from the reception circuit section by driving the reception circuit section at a second drive timing delayed as much as a half cycle of a switching noise in the switching power supply from the first drive timing, and performing an addition process on the first processed signal and the second processed signal.

In this application example, similarly to the application examples described above, since the switching noise to be superimposed on the first processed signal and the switching noise to be superimposed on the second processed signal are shifted as much as a half cycle form each other, by adding the first processed signal and the second processed signal to each other, the switching noise can be reduced. Thus, the measurement result of the highly accurate ultrasonic measurement can be obtained.

BRIEF DESCRIPTION OF THE DRAWINGS

The invention will be described with reference to the accompanying drawings, wherein like numbers reference like elements.

FIGS. 12A through 12D are timing charts of a switching cycle of a switching power supply, a frame timing signal, a transmission timing signal of an ultrasonic wave, and a reception timing signal of the ultrasonic wave of the third embodiment.

DESCRIPTION OF EXEMPLARY EMBODIMENTS

First Embodiment

A first embodiment of the invention will hereinafter be described based on the accompanying drawings.

Figure 1:
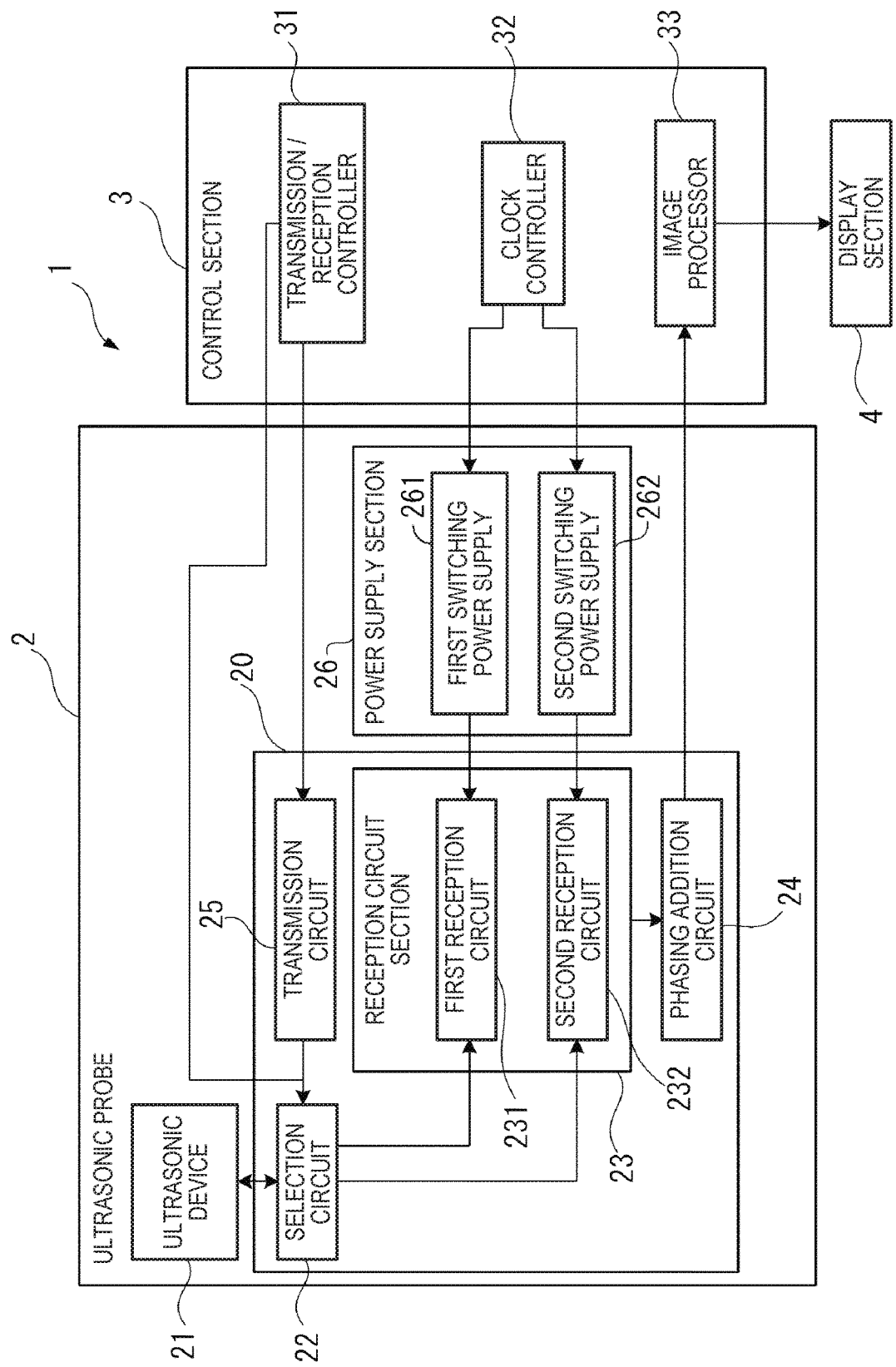
FIG. 1 is a block diagram showing a schematic configuration of an ultrasonic apparatus according to a first embodiment of the invention.

FIG. 1 is a block diagram showing a schematic configuration of an ultrasonic apparatus according to the present embodiment.

As shown in FIG. 1, the ultrasonic apparatus 1 according to the present embodiment is configured including an ultrasonic probe 2 (an ultrasonic module), a control section 3, and a display section 4. It should be noted that it is possible to adopt a configuration in which the ultrasonic probe 2, the control section 3, and the display section 4 are configured as separate bodies, or a configuration in which the ultrasonic probe 2, the control section 3, and the display section 4 are incorporated in, for example, a housing to form a unit.

The ultrasonic apparatus 1 transmits an ultrasonic wave from an ultrasonic device 21 of an ultrasonic probe 2 to an object such as a living body, and then receives the ultrasonic wave reflected by an internal tissue of the object with the ultrasonic device 21. Then, the ultrasonic apparatus 1 processes the received signal, which is output when the ultrasonic device 21 receives the ultrasonic wave, with a reception circuit 23 to form an echo signal, and then performs an addition process on the echo signal with a phasing addition circuit 24. Then, the control section 3 generates the internal tomographic image (a B-mode image) of the object based on an addition signal on which the addition process has been performed by the phasing addition circuit, and then makes the display section 4 display the internal tomographic image thus generated.

Hereinafter, each of the constituents of the ultrasonic apparatus 1 will be described in detail.
Configuration of Ultrasonic Probe 2

As shown in FIG. 1, the ultrasonic probe 2 is provided with the ultrasonic device 21, a transmission/reception section 20 (a wiring board), and a power supply section 26. Further, the transmission/reception section 20 is provided with a selection circuit 22, the reception circuit 23, the phasing addition circuit 24, and a transmission circuit 25.
Configuration of Ultrasonic Device FIG. 2 is a cross-sectional view showing a schematic configuration of the ultrasonic device 21 according to the present embodiment.

Figure 3:
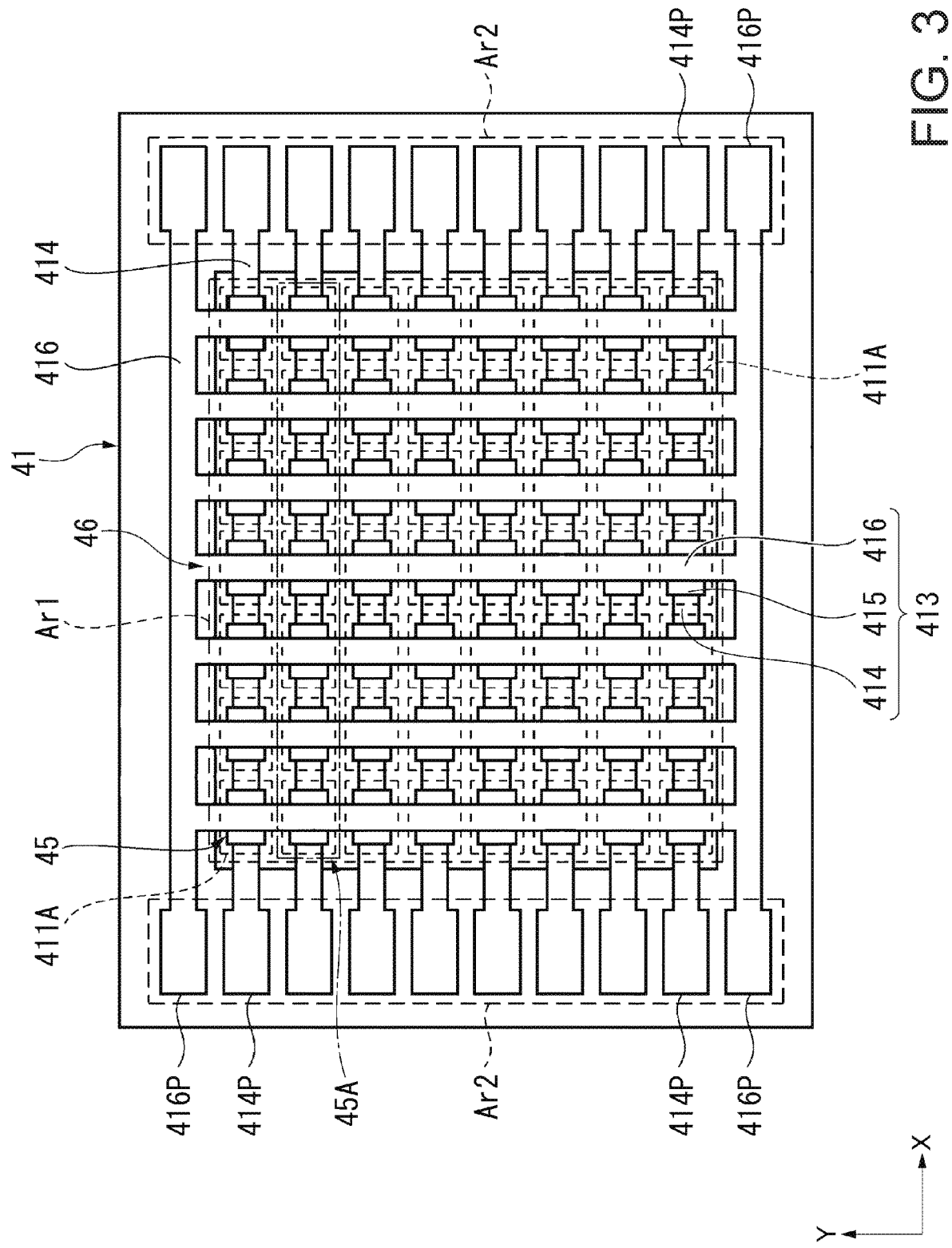
FIG. 3 is a plan view showing a schematic configuration of an element substrate in the ultrasonic device according to the first embodiment.

FIG. 3 is a plan view showing a schematic configuration of an element substrate 41 in the ultrasonic device 21.

Figure 2:
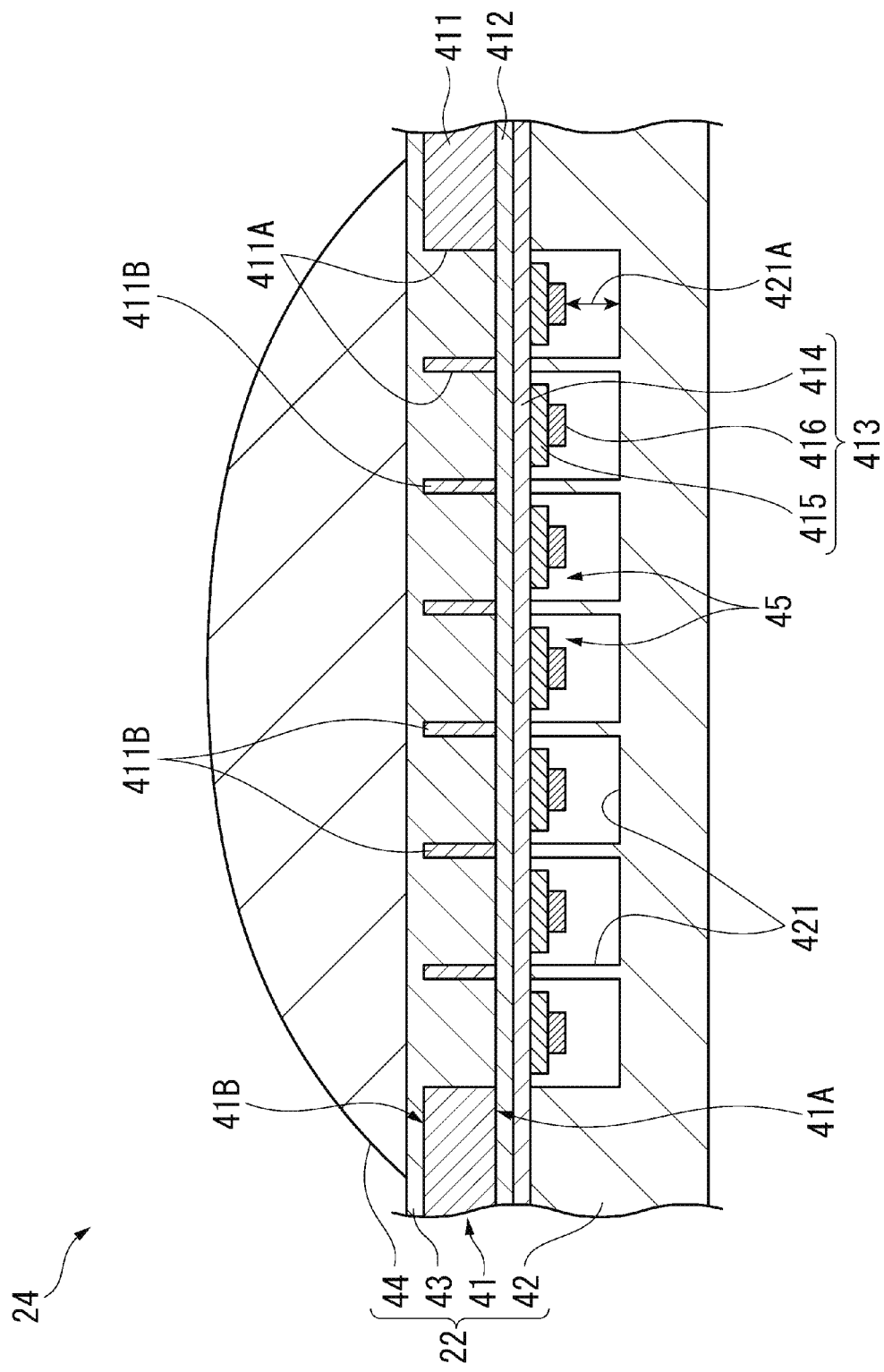
FIG. 2 is a cross-sectional view showing a schematic configuration of the ultrasonic device according to the first embodiment.

As shown in FIG. 2, the ultrasonic device 21 is constituted by the element substrate 41, a sealing plate 42, an acoustic matching layer 43, and an acoustic lens 44.

As shown in FIG. 2, the element substrate 41 is provided with a substrate main body part 411, a vibrating film 412 disposed on the sealing plate 42 side of the substrate main body part 411, and piezoelectric elements 413 stacked on the vibrating film 412. In the element substrate 41, a central area of the element substrate 41 is provided with an array region Ar1 in a planar view viewed from the thickness direction of the substrate shown in FIG. 3, and in the array region Ar1, a plurality of ultrasonic elements 45 is arranged in a matrix.

The substrate main body part 411 is a semiconductor substrate made of, for example, Si. Inside the array region Ar1 in the substrate main body part 411, there are disposed aperture parts 411A corresponding respectively to the ultrasonic elements 45. Further, the aperture parts 411A are closed by the vibrating film 412 disposed on the rear surface 41A side (the sealing plate 42 side) of the substrate main body part 411.

The vibrating film 412 is formed of, for example, $SiO_2$ or a laminated body of $SiO_2$ and $ZrO_2$, and is disposed so as to cover the entire area on the rear surface 41A side of the substrate main body part 411. The thickness dimension of the vibrating film 412 becomes sufficiently small one with respect to the substrate main body part 411.

Further, as shown in FIG. 2, on the vibrating film 412, which closes each of the aperture parts 411A, there are disposed the piezoelectric elements 413 each of which is a laminated body of a lower-part electrode 414, a piezoelectric film 415, and an upper-part electrode 416. Here, the vibrating film 412, which closes the aperture part 411A and the piezoelectric element 413 constitute a single ultrasonic element 45.

In such an ultrasonic element 45, by applying a rectangular-wave voltage having a predetermined cycle between the lower-part electrode 414 and the upper-part electrode 416, it is possible to vibrate the vibrating film 412 in an aperture region of each of the aperture parts 411A to transmit the ultrasonic wave. Further, when the vibrating film 412 is vibrated by the ultrasonic wave reflected by the object, a potential difference occurs between an upper part and a lower part of the piezoelectric film 415. Therefore, by detecting the potential difference occurring between the lower-part electrode 414 and the upper-part electrode 416, it becomes possible to detect the ultrasonic wave received.

Further, in the present embodiment, as shown in FIG. 3, the ultrasonic array 46 is configured by arranging a plurality of such ultrasonic elements 45 as described above in the predetermined of array region Ar1 of the element substrate 41 along an X direction (a slicing direction) and a Y direction (a scanning direction, which is one direction according to the invention) crossing (perpendicular to, in the present embodiment) the X direction.

Here, the lower-part electrode 414 is formed to be shaped like a straight line along the X direction. In other words, the lower-part electrode 414 is disposed straddling a plurality of ultrasonic elements 45 arranged along the X direction, and constitutes a first electrode pad 414P in each of terminal regions Ar2 outside the array region Ar1.

On the other hand, the upper-part electrode 416 is connected between the piezoelectric elements 413 in the array region Ar1. A part of the upper-part electrode 416 is extracted to each of the terminal regions Ar2 to form a second electrode pad 416P.

In such a configuration, there is formed the ultrasonic array 46 having a one-dimensional array structure in which the ultrasonic elements 45 connected by the lower-part electrode 414 to each other and arranged in the X direction constitute one ultrasonic element group 45A, and the plurality of ultrasonic element groups 45A is arranged along the Y direction.

The sealing plate 42 is bonded to the element substrate 41 on the back surface 41A side, and reinforces the strength of the element substrate 41. The sealing plate 42 is provided with a plurality of concave grooves 421, which correspond respectively to the aperture parts 411A of the element substrate 41, formed in an area opposed to the array region Ar1 of the element substrate 41. Thus, it results that a gap having a predetermined dimension is provided between the element substrate 41 and the area (inside the aperture part 411A) vibrated by the ultrasonic element 45 in the vibrating film 412, and thus, the vibration of the vibrating film 412 is prevented from being hindered. Further, it is possible to suppress the problem (cross talk) that the back wave from one ultrasonic element 45 enters another ultrasonic element 45 adjacent to that ultrasonic element 45.

Further, when the vibrating film 412 vibrates, an ultrasonic wave is also emitted toward the sealing plate 42 side (the rear surface 41A side) as the back wave in addition to the aperture part 411A side (the operation surface 41B side). The back wave is reflected by the sealing plate 42, and is then emitted again toward the vibrating film 412 side via the gap. On this occasion, if the phase of the reflected back wave and the phase of the ultrasonic wave emitted from the vibrating film 412 toward the operation surface 41B side are shifted from each other, the ultrasonic wave is attenuated. Therefore, in the present embodiment, the groove depth of each of the concave grooves 421 is set so that the acoustic distance in the gap becomes an odd multiple of a quarter ($\lambda/4$) of the wavelength $\lambda$ of the ultrasonic wave. In other words, the thickness dimensions of the variety of parts of the element substrate 41 and the sealing plate 42 are set taking the wavelength $\lambda$ of the ultrasonic wave emitted from the ultrasonic elements 45 into consideration.

As shown in FIG. 2, the acoustic matching layer 43 is disposed on the operation surface 41B side of the element substrate 41. Specifically, the acoustic matching layer 43 is formed so as to fill in the aperture parts 411A of the element substrate 41, and to have a predetermined thickness dimension from the operation surface 41B side of the substrate main body part 411.

The acoustic lens 44 is disposed on the acoustic matching layer 43, and the surface of the acoustic lens 44 forms an ultrasonic wave transmitting/receiving end surface.

The acoustic matching layer 43 and the acoustic lens 44 efficiently propagate the ultrasonic wave, which has been emitted from the ultrasonic elements 45, to the object, and further propagate the ultrasonic wave, which has been reflected in the object, to the ultrasonic elements 45 with efficiency. Therefore, the acoustic matching layer 43 and the acoustic lens 44 are set to have an acoustic impedance intermediate between the acoustic impedance of the ultrasonic elements 45 of the element substrate 41 and the acoustic impedance of the object. In the case in which the object is a living body, as a material having such an acoustic impedance as described above, there can be cited, for example, silicone.

Such an ultrasonic device 21 as described above is disposed on the transmission/reception section 20, and the electrode pads 414P, 416P are respectively connected to connection terminals disposed on the transmission/reception section 20. Here, the second electrode pads 416P are connected to a reference potential circuit, and are set to a reference potential (e.g., 0 potential). On the other hand, the connection terminals to which the first electrode pads 414P are connected are connected to the selection circuit 22.

Configuration of Transmission/Reception Section 20 and Power Supply Section 26

Hereinafter, the selection circuit 22, the reception circuit 23, the power supply section 26 for supplying the reception circuit 23 and so on with the electrical power, the phasing addition circuit 24, and the transmission circuit 25 provided to the transmission/reception circuit 20 will be described. Further, although not shown in the drawings, the transmission/reception section 20 is provided with a switch circuit and so on having a function of performing clamping so that a signal equal to or higher than a predetermined voltage does not enter the reception circuit 23 when performing the transmission process of the ultrasonic wave.

The selection circuit 22 is a switching circuit for changing the connection state between the connection terminals (drive connection terminals) connected to the first electrode pads 414P, and the reception circuit 23 and the transmission circuit 25. Specifically, when performing the transmission process of transmitting the ultrasonic wave from the ultrasonic device 21, the selection circuit 22 connects the drive connection terminals and the transmission circuit 25 to each other. Further, when performing the reception process of receiving the ultrasonic wave from the object, the selection circuit 22 connects the drive connection terminals and the reception circuit 23 to each other.

The reception circuit 23 is configured including a first reception circuit 231 and a second reception circuit 232.

Figure 4:
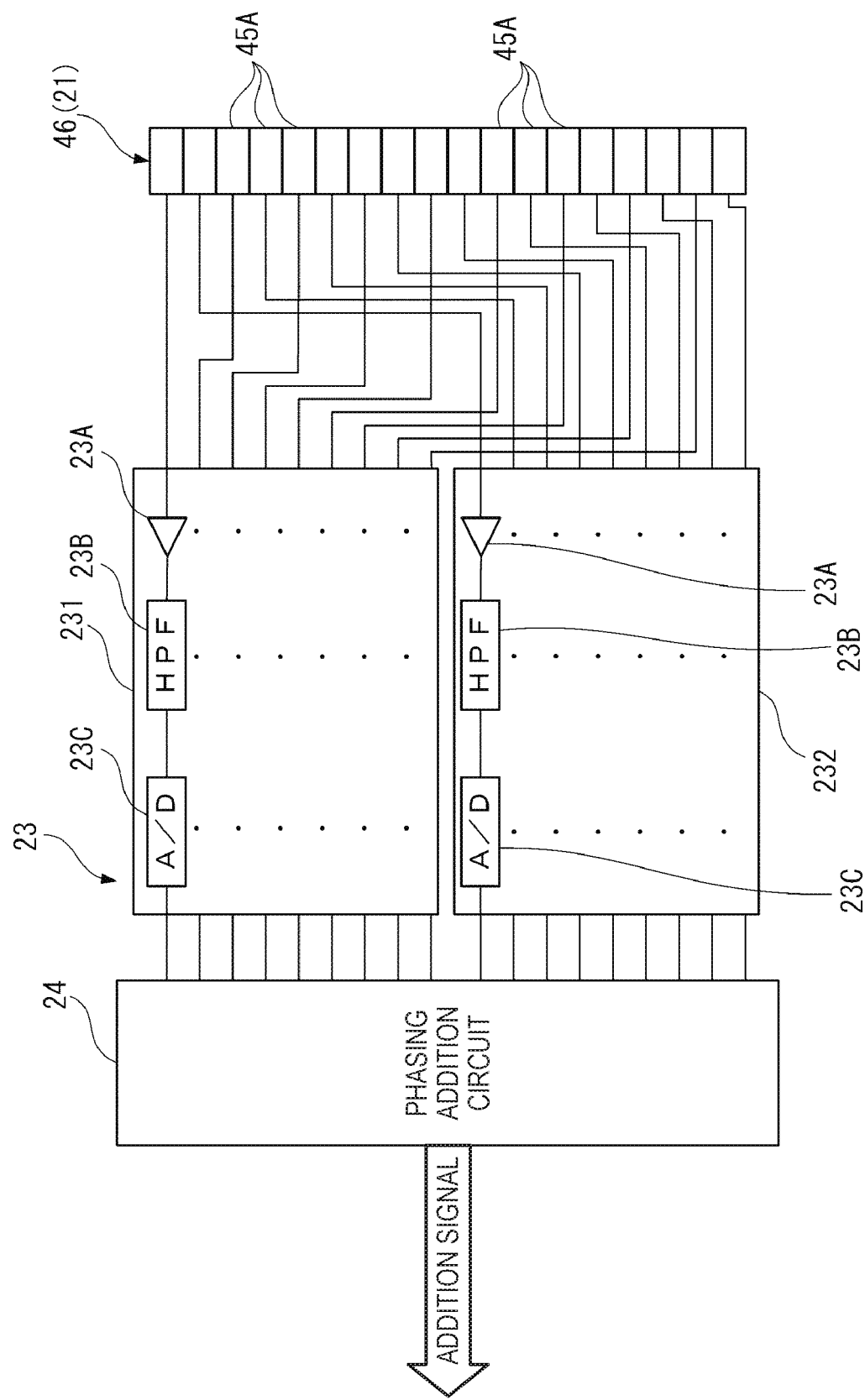
FIG. 4 is a diagram showing a connection relationship between a first reception circuit and a second reception circuit of a reception circuit section, and ultrasonic element groups of the ultrasonic device.

FIG. 4 is a diagram showing a connection relationship between the reception circuits 231, 232 of the reception circuit 23 and the ultrasonic element groups 45A of the ultrasonic device 21. It should be noted that the illustration of the selection circuit 22 is omitted in FIG. 4.

As shown in FIG. 1 and FIG. 4, the reception circuit 23 is provided with the first reception circuit 231 and the second reception circuit 232. The first reception circuit 231 is electrically connected to odd-numbered ultrasonic element groups 45A out of the ultrasonic element groups 45A arranged in the scanning direction of the ultrasonic device 21. Further, the second reception circuit 232 is electrically connected to even-numbered ultrasonic element groups 45A out of the ultrasonic element groups 45A arranged in the scanning direction of the ultrasonic device 21.

The first reception circuit 231 is provided with a plurality of reception sections disposed so as to correspond respectively to the odd-numbered ultrasonic element groups 45A. These reception sections are each a circuit for generating an echo signal (a digital signal) from the reception signal (an analog signal) input from each of the ultrasonic element groups 45A, and are each specifically provided with an amplifier 23A, a high-pass filter (HPF 23B), and an A/D converter (A/D 23C).

The second reception circuit 232 also has substantially the same configuration, and is provided with a plurality of reception sections disposed so as to correspond respectively to the even-numbered ultrasonic element groups 45A, and these reception sections are each provided with the amplifier 23A, the high-pass filter (HPF 23B), and the A/D converter (A/D 23C).

The reception signals processed by the respective reception sections of the first reception circuit 231 are each output to the phasing addition circuit 24 as a first echo signal. In the present embodiment, the first echo signal corresponds to a first processed signal according to the invention.

Further, the reception signals processed by the respective reception sections of the second reception circuit 232 are each output to the phasing addition circuit 24 as a second echo signal. In the present embodiment, the second echo signal corresponds to a second processed signal according to the invention.

Further, the first reception circuit 231 and the second reception circuit 232 are driven by the electrical power supplied from the power supply section 26.

Specifically, the power supply section 26 is provided with a first switching power supply 261 and a second switching power supply 262. The first switching power supply 261 and the second switching power supply 262 have substantially the same configurations. Specifically, these switching power supplies 261, 262 each stably supply the drive voltage with an ON-OFF switching cycle (switching cycle) due to ON-OFF control by a semiconductor switching element.

Incidentally, in such switching power supplies 261, 262, there are generated first through $N^{th}$-order switching noises. Here, although the noise with a low frequency out of the band is cut by the HPF 23B, it results that the $N^{th}$-order switching noise within the band remains uncut by the HPF 23B. Therefore, it results that the $N^{th}$-order switching noise is superimposed also on the echo signals (the first echo signal, the second echo signal) from the reception circuits 231, 232 supplied with the electrical power from the power supply section 26. Although the higher the order is ($N^{th}$ order), the smaller the switching noise is, the switching noise is grown by the superimposition by the phasing addition to cause the artifacts.

Here, in the present embodiment, due to the control by the control section 3 described later, the drive timing (a first drive timing) of the first switching power supply 261 and the drive timing (a second drive timing) of the second switching power supply 262 are shifted as much as a half cycle of the switching noise described above. In other words, the first switching power supply 261 is driven at the first drive timing, and then the second switching power supply 262 is driven at the second drive timing delayed as much as a half cycle of the switching noise.

Therefore, the switching noise to be superimposed on the second echo signal output from the second reception circuit 232 is superimposed so as to be delayed as much as a half cycle of the switching noise with respect to the switching noise to be superimposed on the first echo signal output from the first reception circuit 231.

The phasing addition circuit 24 performs the phasing addition process on the first echo signal input from the first reception circuit 231 and the second echo signal input from the second reception circuit 232, and then outputs an addition signal to the control section 3. On this occasion, the phasing addition circuit 24 performs the addition process on the echo signals by performing addition while appropriately adjusting the phases of the echo signals in accordance with a distance between a measurement position (an ultrasonic wave reflection position) in the depth direction and each of the ultrasonic element groups 45A, a transmission timing of the ultrasonic wave, and so on. Therefore, in the present embodiment, the phasing addition circuit 24 corresponds to a signal adding section according to the invention.

Here, in the case in which the ultrasonic wave is reflected at the reflection position in the vicinity of the ultrasonic device 21, an angle defined by a line segment connecting the reflection position and each of the ultrasonic element groups 45A becomes large. Therefore, in the vicinity of the ultrasonic device 21, a relatively long delay occurs in the reception timing of the ultrasonic wave in each of the ultrasonic element groups 45A. Therefore, in the case of performing the phasing addition on the echo signals (the first echo signal, the second echo signal), the phase shift amount of each of the echo signals becomes relatively large when performing the phasing process. In this case, even if the switching noise is superimposed on each of the echo signals as described above, it results that the switching noise is dispersed, and the influence of the switching noise becomes in a negligible level.

In contrast, in the case in which the ultrasonic wave is reflected at the reflection position far (with a distance equal to or longer than a predetermined value) from the ultrasonic device 21, an angle defined by a line segment connecting the reflection position and each of the ultrasonic element groups 45A becomes small. In this case, the reception timings of the ultrasonic wave in the respective ultrasonic element groups 45A become roughly the same as each other (a delay hardly occurs). Therefore, in the case of performing the phasing addition on the echo signals (the first echo signal, the second echo signal), the phase shift amount of each of the echo signals becomes relatively small, and the switching noise described above is not dispersed when performing the phasing process.

Figure 5:
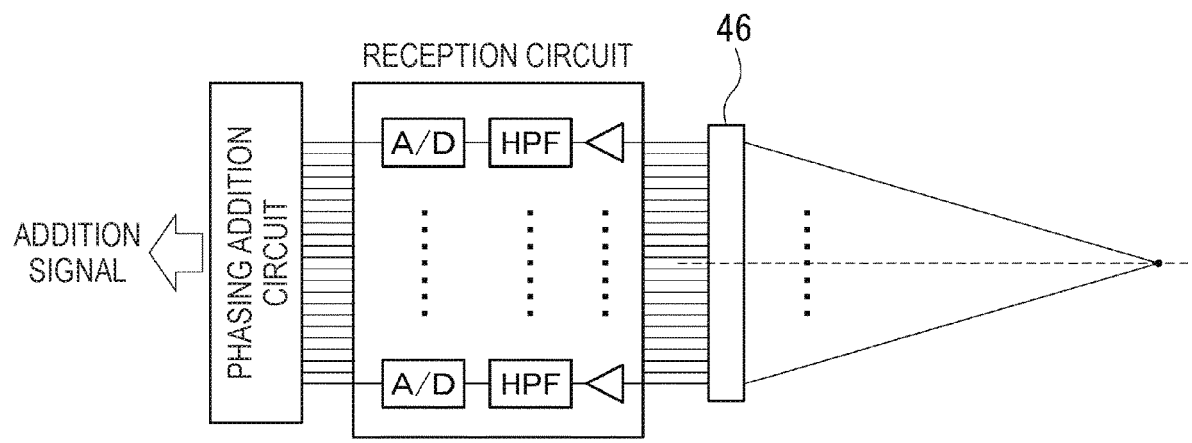
FIG. 5 is a diagram showing a reception circuit and a phasing addition circuit of the related art.
Figure 6:
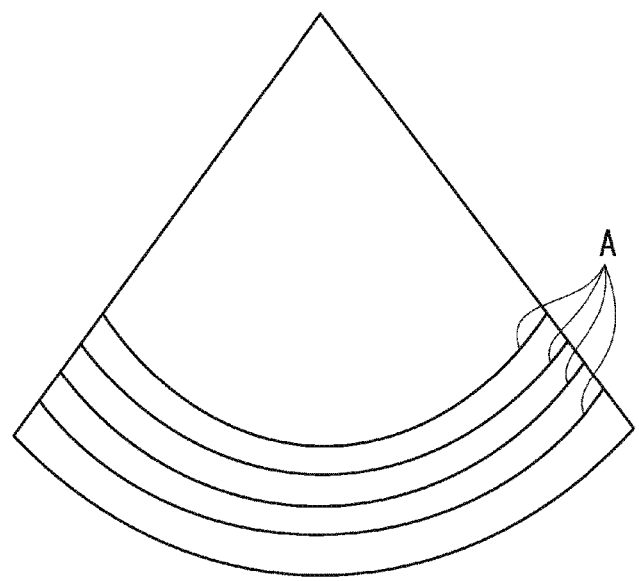
FIG. 6 is a diagram showing an example of an internal tomographic image of an object generated based on an addition signal processed by the circuits shown in FIG. 5.

FIG. 5 is a diagram showing a reception circuit and a phasing addition circuit of the related art. Further, FIG. 6 is an example of an internal tomographic image generated based on the addition signal processed by the circuit shown in FIG. 5.

Here, in such a related art reception circuit as shown in FIG. 5, the switching noise is superimposed at substantially the same positions of the respective echo signals output from the reception circuit section. In this case, when the echo signals are added in the phasing addition circuit, the switching noise components are added to each other, and thus, the artifacts A are generated in the internal tomographic image as shown in FIG. 6.

Figure 7:
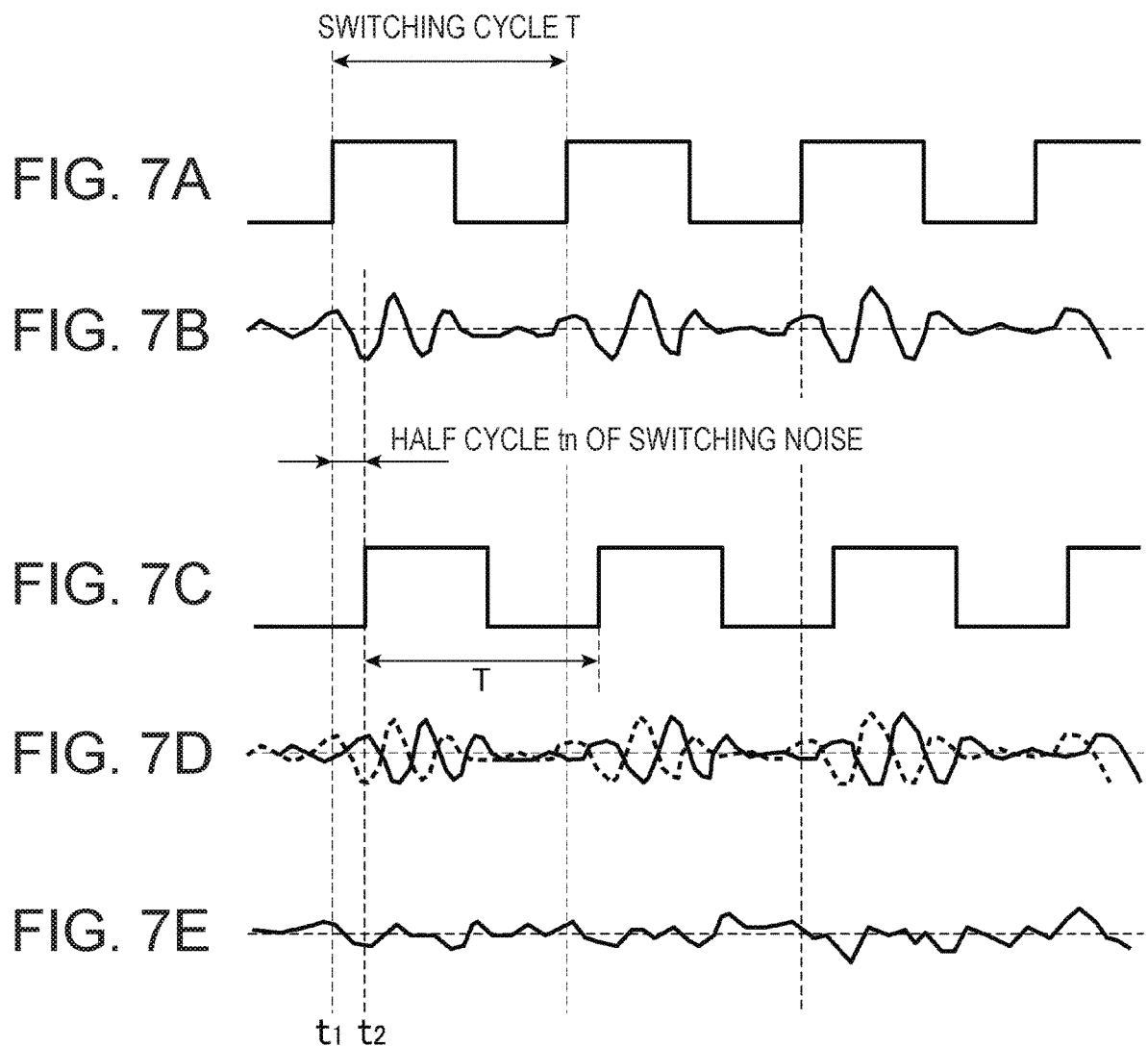
FIG. 7A is a diagram showing a switching cycle of a first switching power supply in the first embodiment.
FIG. 7B is a diagram showing a signal waveform of a first echo signal.
FIG. 7C is a diagram showing a switching cycle of a second switching power supply 262.
FIG. 7D is a diagram showing a signal waveform of a second echo signal.
FIG. 7E is a diagram showing a signal waveform of the addition signal.

FIG. 7A is a diagram showing a switching cycle of the first switching power supply 261 in the present embodiment, FIG. 7B is a diagram showing a signal waveform of the first echo signal, FIG. 7C is a diagram showing a switching cycle of the second switching power supply 262, FIG. 7D is a diagram showing a signal waveform of the second echo signal, and FIG. 7E is a diagram showing a signal waveform of the addition signal. The dotted line in FIG. 7D shows the first echo signal.

In the present embodiment, as shown in FIGS. 7A and 7C, after the first switching power supply 261 is driven (a first drive timing) with a switching cycle T, the second switching power supply 262 is then driven at a second drive timing, which is delayed as much as a half cycle of the switching noise, with the same switching cycle T as that of the first switching power supply 261. It should be noted that in the example shown in FIGS. 7A through 7E, the switching noises of the switching third-order cycle are superimposed.

Therefore, as shown in FIGS. 7B and 7D, the switching noise superimposed on the second echo signal is also delayed as much as a half cycle with respect to the switching noise superimposed on the first echo signal.

Therefore, if the addition process is performed on the first echo signal and the second echo signal in the phasing addition circuit 24, the switching noises are cancelled out with each other to be attenuated as shown in FIG. 7E.

The transmission circuit 25 outputs a drive signal (a pulse signal) to each of the ultrasonic element groups 45A of the ultrasonic device 21 based on the control by the control section 3. Thus, the ultrasonic wave is output from each of the ultrasonic element groups 45A. On this occasion, by sequentially delaying the drive signals output to the ultrasonic element groups 45A, it becomes possible to control the output direction of the ultrasonic wave transmitted from the ultrasonic device 21.

Configuration of Control Section 3

The control section 3 is configured including a storage section such as a memory and an arithmetic circuit such as a central processing unit (CPU), and reads and executes a variety of types of programs stored in the memory to thereby function as a transmission/reception controller 31, a clock controller 32, and an image processor 33 as shown in FIG. 1.

The transmission/reception controller 31 outputs a drive command signal to the selection circuit 22 and the transmission circuit 25 when an operation signal instructing to perform ultrasonic measurement is input from, for example, an operation unit (not shown).

The clock controller 32 outputs a clock signal to the first switching power supply 261 and the second switching power supply 262. Specifically, the clock controller 32 outputs the clock signal, which instructs to start the drive with the switching cycle T at the first drive timing t1 (see FIGS. 7A through 7E), to the first switching power supply 261. Further, the clock controller 32 outputs the clock signal, which instructs to start the drive with the switching cycle T at the second drive timing t2 delayed as much as a half cycle to of the switching noise from the first drive timing t1, to the second switching power supply 262.

The image processor 33 is an image processing section according to the invention, and generates the internal tomographic image based on the addition signals input from the phasing addition circuit 24.

Method of Driving Ultrasonic Apparatus 1

Then, an ultrasonic measurement method (the drive method) using such an ultrasonic apparatus 1 as described above will be described.

Figure 8:
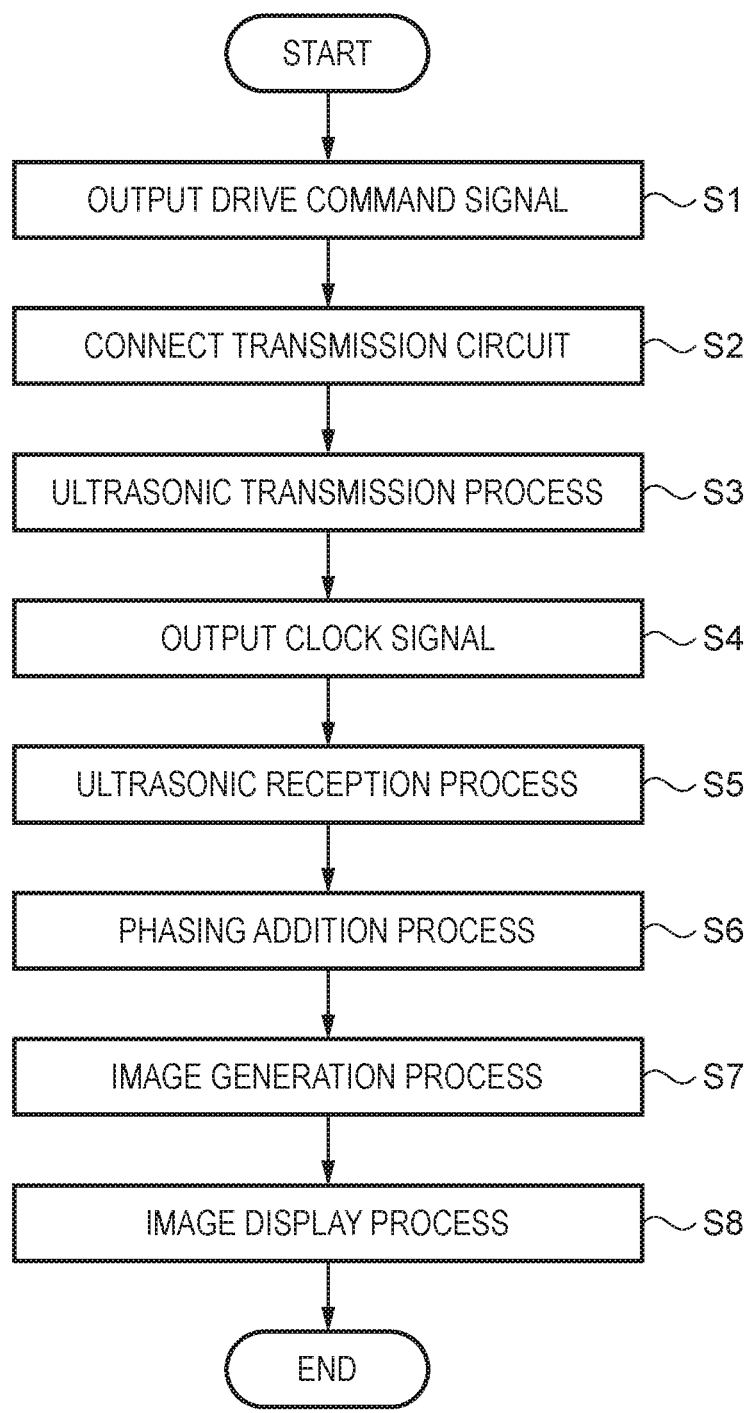
FIG. 8 is a flowchart showing a method of driving the ultrasonic apparatus according to the first embodiment.

FIG. 8 is a flowchart showing a method of driving the ultrasonic apparatus 1 according to the present embodiment.

When the operation signal instructing to start the ultrasonic measurement from, for example, an operation unit not shown to the ultrasonic apparatus 1, the transmission/reception controller 31 of the control section 3 generates the drive command signal, and then outputs (step S1) the drive command signal to the ultrasonic probe 2.

Firstly, the selection circuit 22 of the ultrasonic probe 2 connects (step S2) the drive connection terminals (the connection terminals to be connected to the first electrode pads 414P) and the transmission circuit 25 to each other based on the drive command signal.

Then, the transmission circuit 25 applies the drive signal to the ultrasonic element groups 45A based on the drive command signal to transmit (step S3) the ultrasonic wave. On this occasion, by applying the drive signal with a delay to the ultrasonic element group 45A, the output timing of the ultrasonic wave of each of the ultrasonic element groups 45A is delayed, and thus, it becomes possible to change the output direction of the ultrasonic wave along the scanning direction. Therefore, the measurement range having a sector shape centered on the ultrasonic array 46 can be scanned with the ultrasonic wave.

Further, when the drive command signal is output from the transmission/reception controller 31 to the ultrasonic probe 2 in the step S1, the clock controller 32 outputs (step S4) the clock signal to the first switching power supply 261 and the second switching power supply 262. Specifically, as described above, the clock controller 32 outputs the clock signal to the first switching power supply 261 at the first drive timing t1, and outputs the clock signal to the second switching power supply 262 at the second drive timing t2 delayed as much as a half cycle to of the switching noise from the first drive timing t1.

It should be noted that the process in step S4 can be performed at the same time as the step S1, and can be performed at any timing prior to the execution of an ultrasonic reception process (step S5) described later.

After the transmission process of the ultrasonic wave in the step S3, the selection circuit 22 connects the drive connection terminals and the reception circuit 23 to each other based on the drive command signal from the control section 3. Thus, as shown in FIG. 4, the odd-numbered ultrasonic element groups 45A arranged in the scanning direction are connected to the first reception circuit 231, and the even-numbered ultrasonic element groups 45A are connected to the second reception circuit 232. In other words, the odd-numbered ultrasonic element groups 45A constitute a first ultrasonic reception section according to the invention, and the even-numbered ultrasonic element groups 45A constitute a second ultrasonic reception section according to the invention.

Further, when the ultrasonic wave transmitted in step S3 is reflected by an internal tissue of the object, the reflected ultrasonic wave is received by each of the ultrasonic element groups 45A, and the reception signal is input (step S5) to the reception circuit 23 (the first reception circuit 231, the second reception circuit 232).

Then, the first echo signal processed in the first reception circuit 231 and the second echo signal processed in the second reception circuit 232 are input to the phasing addition circuit 24, and the phasing addition circuit 24 performs (step S6) the phasing addition process on these echo signals.

On this occasion, due to the step S4, the first reception circuit 231 is supplied with the electrical power with the switching cycle T from the first drive timing t1, and the second reception circuit 232 is supplied with the electrical power with the switching cycle T from the second drive timing t2. Therefore, the switching noise to be superimposed on the first echo signal output from the first reception circuit 231 and the switching noise to be superimposed on the second echo signal output from the second reception circuit 232 appear at respective timings shifted as much as a half cycle of the switching noise from each other as shown in FIGS. 7B and 7C.

Therefore, as shown in FIG. 7E, it results that the addition signal with the switching noises attenuated is output when adding these echo signals to each other.

Then, when the phasing addition process is performed by the phasing addition circuit 24, and the addition signal is input to the control section 3, the image processor 33 generates (step S7) the internal tomographic image of the object based on the addition signal, and makes the display section 4 display (step S8) the internal tomographic image.

It should be noted that since a related art method can be used as the image generation process based on the addition signal, the description of the image generation process is omitted here.

Functions and Advantages of Present Embodiment

In the ultrasonic apparatus 1 according to the present embodiment, the ultrasonic probe 2 (the ultrasonic module) is provided with the reception circuit 23 receiving the reception signal from the ultrasonic device 21 for receiving the ultrasonic wave, and then generating the echo signals. The reception circuit 23 is provided with the first reception circuit 231 and the second reception circuit 232, and the first reception circuit 231 is driven by the first switching power supply 261 with the switching cycle T from the first drive timing t1, and outputs the first echo signal. Further, the second reception circuit 232 is driven by the second switching power supply 262 with the switching cycle T from the second drive timing delayed as much as a half cycle tn of the switching noise from the first drive timing, and outputs the second echo signal.

Therefore, the switching noise to be superimposed on the first echo signal and the switching noise to be superimposed on the second echo signal are shifted as much as a half cycle tn of the switching noise from each other. Therefore, if the phasing addition circuit 24 performs the addition process on the first echo signal and the second echo signal, the switching noises are cancelled out with each other to be attenuated. Thus, the switching noise in the addition signal can be suppressed, and the ultrasonic measurement high in accuracy can be performed.

Further, the image processor 33 of the ultrasonic apparatus 1 generates the image based on such an addition signal. In this case, the artifacts caused by the switching noise is not generated in the image generated, and thus, it is possible to generate the internal tomographic image of the object based on the measurement result high in accuracy.

Further, in the present embodiment, by controlling the drive timings of the first switching power supply 261 and the second switching power supply 262, reduction of the switching noise can easily be achieved. Therefore, since the configuration of the filter for removing the noise included in each of the echo signals, or the like can be simplified, and further, a filtering process for removing the switching noise becomes unnecessary in the image processor 33, simplification of the process can also be achieved.

In the ultrasonic probe 2 according to the present embodiment, the ultrasonic device 21 has the plurality of ultrasonic element groups 45A arranged in the scanning direction, the odd-numbered ultrasonic element groups 45A out of these ultrasonic element groups 45A are connected to the first reception circuit 231, and the even-numbered ultrasonic element groups 45A are connected to the second reception circuit 232.

In general, between the ultrasonic element groups 45A, there occurs a delay when receiving the ultrasonic wave having been reflected at a predetermined reflection position. In this case, when phasing the received ultrasonic waves in the phasing addition process by the phasing addition circuit 24, the phase shift amount becomes large in some cases. In such a case, since the switching noise is also shifted as much as a comparable amount, the positions of the switching noises are shifted from each other, and thus, the switching noise cannot sufficiently be attenuated in some cases. In contrast, in the present embodiment, since the addition process is performed on the echo signals of the ultrasonic element groups 45A adjacent to each other, the phase shift amount in the phasing addition process is small, and thus, the switching noise can effectively be reduced.

In the present embodiment, the control section 3 is provided with the clock controller 32 for commanding the drive timings t1, t2 and the switching cycle T of the respective switching power supplies 261, 262.

In general, the switching power supply incorporates a clock, and is driven with the clock cycle output from the clock. However, in this case, since it is necessary to output the clock cycle of the first switching power supply 261 to the second switching power supply 262, and at the same time, to drive the second switching power supply 262 in sync with the timing shifted as much as a half cycle to of the switching noise from the clock cycle thus input, the circuit configuration and the control become complicated. In contrast, in the present embodiment, since the clock controller 32 of the control section 3 controls the drive timings of the first switching power supply 261 and the second switching power supply 262, it is sufficient to command the drive timings to the respective switching power supplies 261, 262, and thus, simplification of the configuration and the process can be achieved.

Second Embodiment

Then, a second embodiment according to the invention will hereinafter be described.

In the first embodiment described above, the odd-numbered ultrasonic element groups 45A are connected to the first reception circuit 231, and the even-numbered ultrasonic element groups 45A are connected to the second reception circuit 232 out of the plurality of ultrasonic element groups 45A arranged in the scanning direction. The present embodiment is different in the point that, in contrast, the ultrasonic element groups 45A to be connected to the first reception circuit 231 and the ultrasonic element groups 45A to be connected to the second reception circuit 232 are separated by the center in the scanning direction, namely between one side and the other side. It should be noted that in the following description, the constituents and the processes having already been described are denoted by the same reference symbols, and the description thereof will be omitted or simplified.

Figure 9:
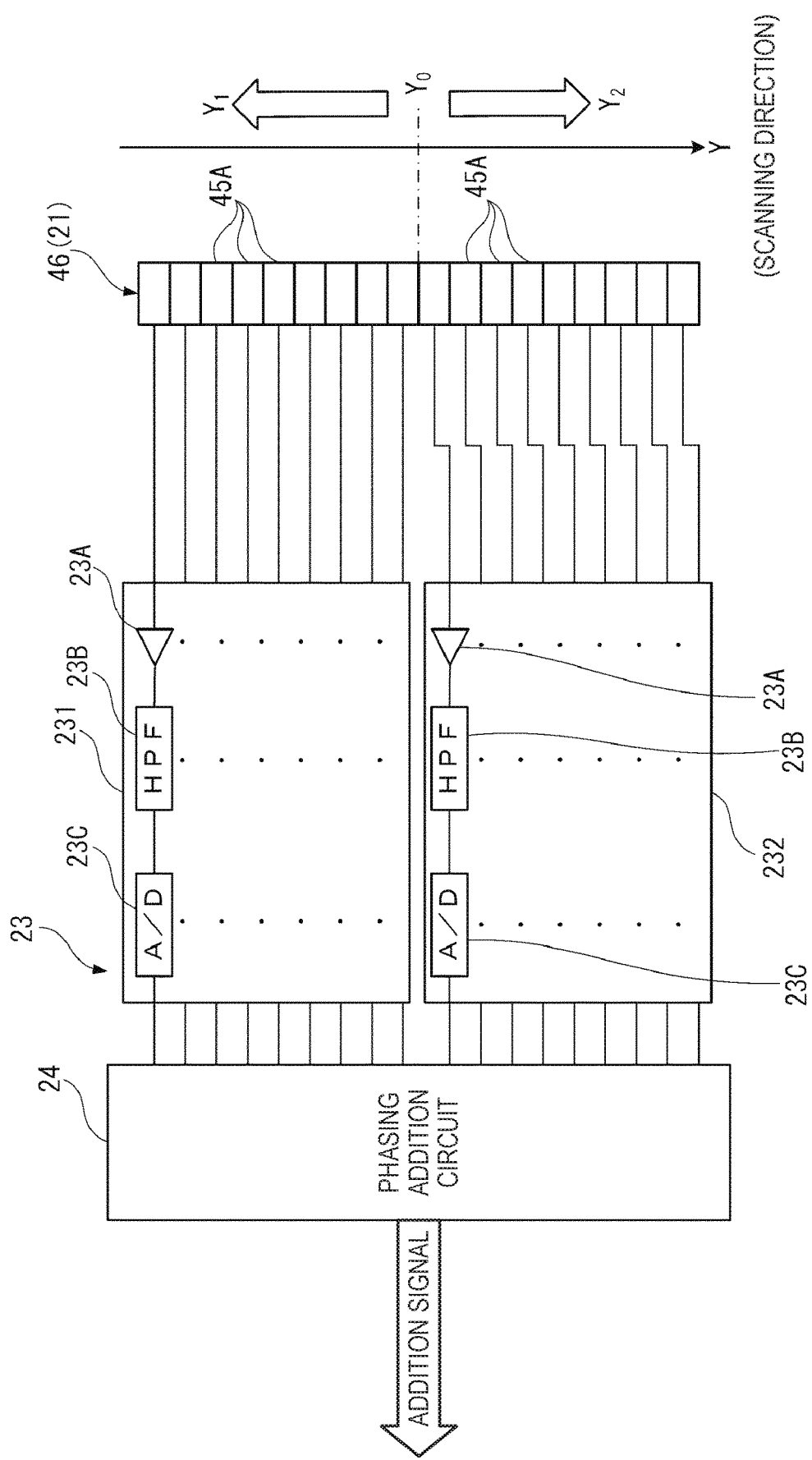
FIG. 9 is a diagram showing a connection relationship between a first reception circuit and a second reception circuit of a reception circuit section, and ultrasonic element groups of the ultrasonic device in a second embodiment of the invention.

FIG. 9 is a diagram showing a connection state between the first reception circuit 231 and the second reception circuit 232 of the reception circuit 23 and the ultrasonic element groups 45A of the ultrasonic device.

As shown in FIG. 9, in the present embodiment, the ultrasonic element groups 45A disposed on the one side (the $Y_1$ side in FIG. 9) from the central position $Y_0$ in the scanning direction (the Y direction) of the ultrasonic array 46 are connected to the first reception circuit 231. Further, the ultrasonic element groups 45A arranged on the other side (the $Y_2$ side in FIG. 9) from the central position $Y_0$ are connected to the second reception circuit 232. In other words, the ultrasonic element groups 45A disposed on the $Y_1$ side constitute the first ultrasonic reception section according to the invention, and the ultrasonic element groups 45A disposed on the $Y_2$ side constitute the second ultrasonic reception section according to the invention.

It should be noted that the rest of the configuration is the same as that of the first embodiment.

In the present embodiment, in the transmission/reception section 20, simplification of the wiring configuration between the drive connection terminals and the reception circuit 23 can be achieved.

Third Embodiment

Then, a third embodiment according to the invention will be described.

In the first embodiment described above, the reception circuit 23 is constituted by the first reception circuit 231 and the second reception circuit 232, the first switching power supply 261 and the second switching power supply 262 are disposed so as to correspond to these reception circuits, and the respective drive timings (the switching cycle) of the first switching power supply 261 and the second switching power supply 262 are shifted from each other to thereby suppress the switching noise. In contrast, the third embodiment is different from the first embodiment described above in the point that the ultrasonic apparatus is configured using a single reception circuit section and a single switching power supply, and the switching noise is reduced by delaying the signal acquisition timing.

Figure 10:
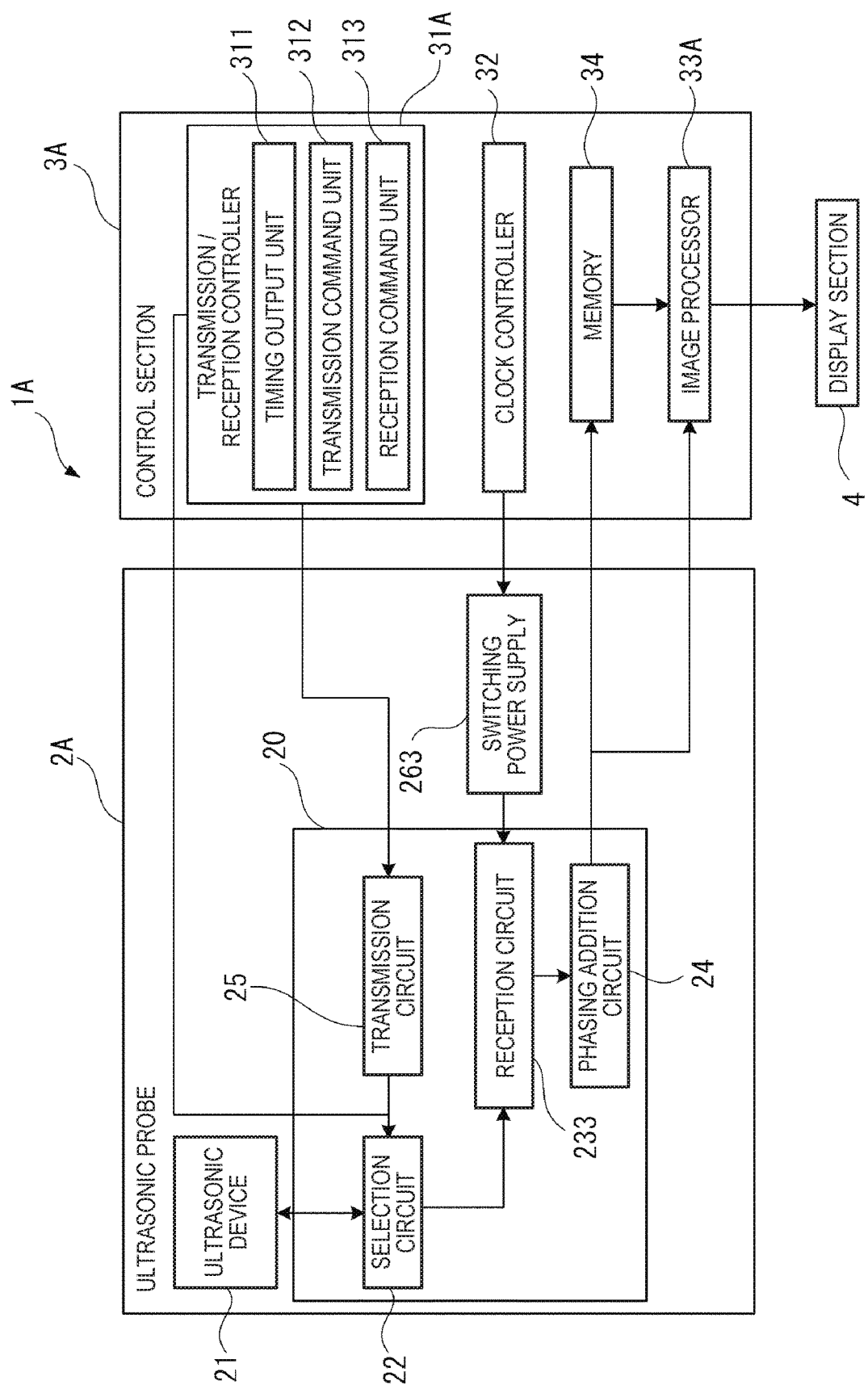
FIG. 10 is a block diagram showing a schematic configuration of an ultrasonic apparatus according to a third embodiment of the invention.

FIG. 10 is a block diagram showing a schematic configuration of an ultrasonic apparatus 1A according to the third embodiment.

As shown in FIG. 10, the ultrasonic apparatus LA according to the present embodiment is provided with an ultrasonic probe 2A, a control section 3A and the display section 4.

The ultrasonic probe 2A is configured including the ultrasonic device 21 having substantially the same configuration as that of the first embodiment, the transmission/reception section 20, and a switching power supply 263.

The transmission/reception section 20 is provided with the selection circuit 22, a reception circuit 233, the phasing addition circuit 24, and the transmission circuit 25. The selection circuit 22, the phasing addition circuit 24, and the transmission circuit 25 have substantially the same configurations as those of the first embodiment.

Further, the reception circuit 233 has substantially the same configuration as the first reception circuit 231 and the second reception circuit 232. In the reception process of the ultrasonic wave, the reception circuit 233 is electrically connected to the drive connection terminals, to which the first electrode pads 414P of the respective ultrasonic element groups 45A, by the selection circuit 22. Further, the reception circuit 233 is provided with a plurality of reception sections (the amplifier 23A, HPF 23B, and A/D 23C) capable of processing the reception signals from the respective ultrasonic element groups 45A.

The reception circuit 233 corresponds to the reception circuit section according to the invention, and is driven by the electrical power supplied from the switching power supply 263. The switching power supply 263 is a switching power supply similar to the first switching power supply 261 and the second switching power supply 262, and is driven with the switching cycle T, and supplies the reception circuit 233 and so on with the electrical power. Also in the present embodiment, by inputting the clock signal from the control section 3A, the switching power supply 263 is driven using the clock cycle of the clock signal as the switching cycle.

It should be noted that in the present embodiment, it is also possible to adopt a configuration in which the switching power supply 263 incorporates the clock. In this case, the clock signal including the clock cycle is input from the switching power supply 263 to the control section 3A.

The control section 3A is configured including a memory 34 and an arithmetic circuit such as a central processing unit (CPU), and reads and executes a variety of types of programs stored in the memory 34 to thereby function as a transmission/reception controller 31A, the clock controller 32, and an image processor 33A as shown in FIG. 10.

The transmission/reception controller 31A constitutes the ultrasonic control section according to the invention, and outputs the drive command signal to the selection circuit 22 and the transmission circuit 25 when an operation signal instructing to perform ultrasonic measurement is input from, for example, an operation unit (not shown) similarly to the first embodiment. Further, the transmission/reception controller 31A performs the transmission process and the reception process of the ultrasonic wave in sync with each other to obtain the echo signal corresponding to a frame of image.

Here, the transmission/reception controller 31A of the present embodiment performs the transmission/reception process of the ultrasonic wave for obtaining the echo signal corresponding to the frame of image a plurality of times while shifting the timing.

Specifically, the transmission/reception controller 31A alternately performs a first frame signal acquisition process for obtaining the echo signal with respect to each of the scanning directions in sync with the switching cycle of the switching power supply 263, and a second frame signal acquisition process for obtaining the echo signal with respect to each of the scanning directions at a timing delayed as much as a half cycle tn of the switching noise from the switching cycle.

Specifically, the transmission/reception controller 31A functions as a timing output unit 311, a transmission command unit 312, and a reception command unit 313.

The timing output unit 311 outputs a first frame timing signal in sync with the switching cycle of the switching power supply 263. The first frame timing signal is a timing signal representing the beginning of the first frame signal acquisition process.

Further, the timing output unit 311 outputs a second frame timing signal at a timing delayed as much as a half cycle tn of the switching noise with respect to the switching cycle of the switching power supply 263 after a predetermined period has elapsed from the output of the first frame timing signal.

Further, the timing output unit 311 outputs the first frame timing signal in sync with the switching cycle of the switching power supply 263 after a predetermined period has elapsed from the output of the second frame timing signal. As described above, the timing output unit 311 alternately outputs the first frame timing signal and the second frame timing signal.

It should be noted that the predetermined period described above is the time related to the first frame signal acquisition process and the second frame signal acquisition process, and is set in accordance with the target area to be scanned with the ultrasonic wave. Specifically, when scanning the target area with the ultrasonic wave, a transmission process of sequentially driving the ultrasonic element groups 45A with a delay to thereby transmit the ultrasonic wave toward the predetermined transmission direction is performed, and then a reception process of receiving the ultrasonic wave having been reflected by the object is performed. In the transmission/reception process described above, by varying the delay time of the drive timing of the ultrasonic element groups 45A in the transmission process, the transmission direction of the ultrasonic wave is varied, and thus, the reception process of the reflected ultrasonic wave with respect to the entire range of the target area is performed. Therefore, the period related to the first frame signal acquisition process and the second frame signal acquisition process corresponds to the period until the processes described above are completed.

The transmission command unit 312 outputs a transmission command instructing to transmit the ultrasonic wave to the ultrasonic probe 2A. The transmission command includes the output direction of the ultrasonic wave, namely the delay information when applying the drive signal to each of the ultrasonic element groups 45A. In response to the input of the transmission command, the selection circuit 22 of the ultrasonic probe 2A connects the drive connection terminals and the transmission circuit 25 to each other to output the drive signal from the transmission circuit 25 to each of the ultrasonic element groups 45A.

The reception command unit 313 outputs a reception command instructing to receive the ultrasonic wave to the ultrasonic probe 2A. In response to the input of the reception command, the selection circuit 22 of the ultrasonic probe 2A connects the drive connection terminals and the reception circuit 233 to each other. Thus, the reception signal is output from the reception circuit 233 to the phasing addition circuit 24, and the addition signal is output from the phasing addition circuit to the control section 3.

It should be noted that the specific operation of the transmission/reception controller 31A will be described later.

The image processor 33A adds a first addition signal based on the first echo signal obtained by the first frame signal acquisition process, and a second addition signal based on the second echo signal obtained by the second frame signal acquisition process to each other to generate an addition processed signal, and then forms an image (an internal tomographic image) based on the addition processed signal.

Here, in the present embodiment, the phasing addition circuit 24 performs the phasing addition process on each of the first echo signals obtained by the first frame signal acquisition process, and the result is output to the control section 3A as the first addition signal. The first addition signal is arbitrarily stored in the memory 34 of the control section 3A.

The first addition signal is a signal obtained by performing the phasing addition process on the reception signals output when the ultrasonic wave reflected at the ultrasonic wave reflection position is received by the respective ultrasonic element groups 45A. In the case of changing the transmission direction for scanning the predetermined target area with the ultrasonic wave, a plurality of first addition signals is obtained with respect to each of the ultrasonic wave reflection positions in the target area.

It should be noted that in the first addition signals, the switching noise superimposed on the first echo signals is superimposed and amplified. In other words, the first addition signals become the signals including the switching noise. In the present embodiment, the first addition signal corresponds to the first processed signal according to the invention.

Further, the phasing addition circuit 24 also performs the phasing addition process on each of the second echo signals obtained by the second frame signal acquisition process similarly to the first echo signal, and the result is output to the control section 3A as the second addition signal. In the second addition signals, the switching noise components in the second echo signals are superimposed and amplified. The switching noise component appears at a position delayed as much as a half cycle to of the switching noise component with respect to the switching noise component in the first addition signal. In the present embodiment, the second addition signal corresponds to the second processed signal according to the invention. The second addition signal is arbitrarily stored in the memory 34 of the control section 3A.

Further, the image processor 33A reads the first addition signal and the second addition signal stored in the memory 34, and then adds the first addition signal and the second addition signal to each other to thereby generate the addition processed signal corresponding to a frame of internal tomographic image. Further, the image processor 33A generates the internal tomographic image based on the addition processed signal thus obtained. On this occasion, the switching noise component included in the first addition signal and the switching noise component included in the second addition signal have the phases shifted as much as a half cycle, and are therefore, cancelled out with each other to be attenuated.

In other words, in the present embodiment, the image processor 33A functions as an image processing section and a signal addition section according to the invention. Further, the ultrasonic module according to the invention is constituted by the ultrasonic probe 2A according to the invention and the control section 3A.

As described above, in the present embodiment, by adding the addition signals (the first addition signal and the second addition signal) corresponding to the two frames of image, the addition processed signal corresponding to a frame of image is generated.

Method of Driving Ultrasonic Apparatus 1A

Then, an ultrasonic measurement method (the drive method) using such an ultrasonic apparatus 1A as described above will be described.

Figure 11:
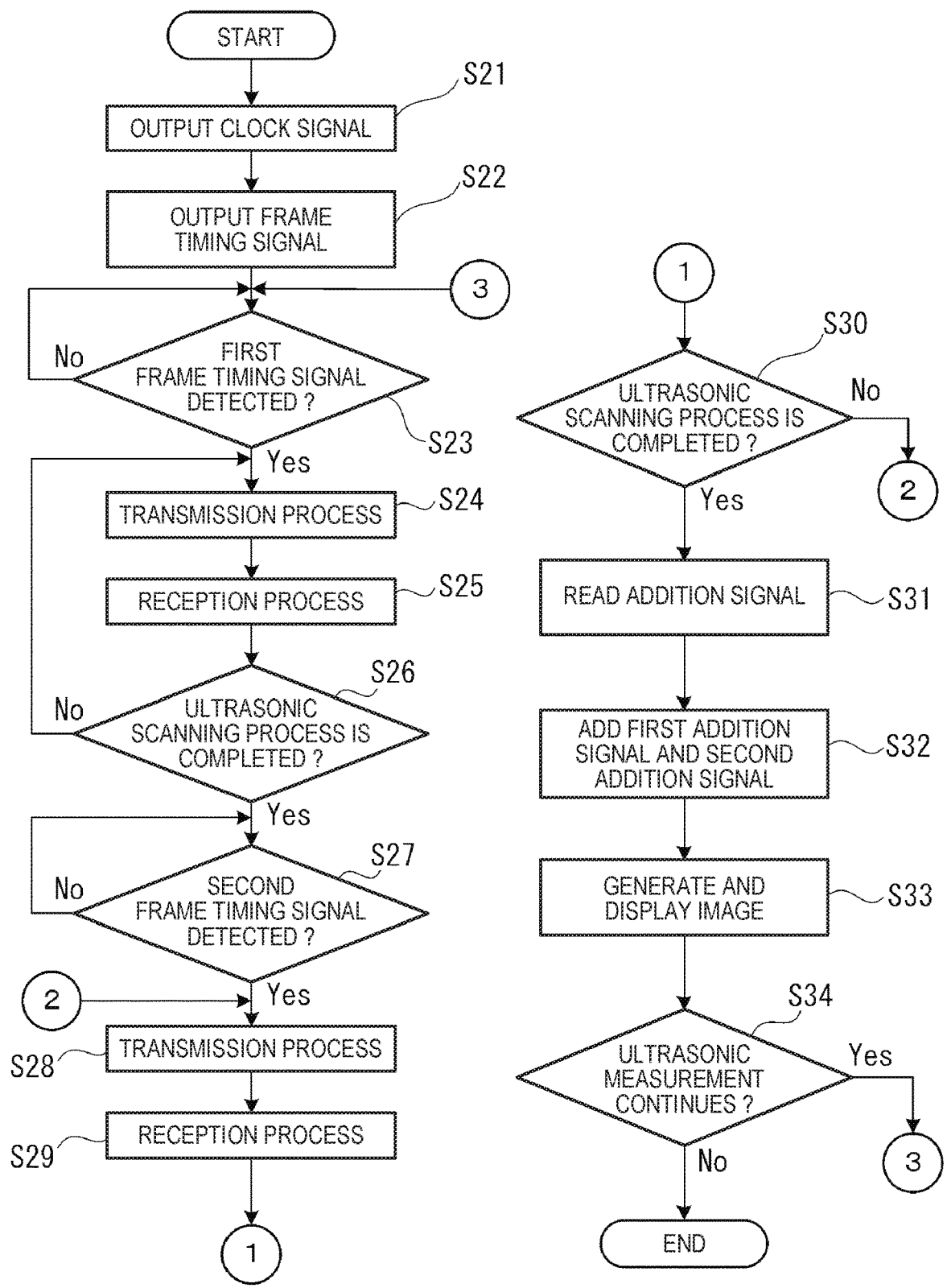
FIG. 11 is a flowchart showing a method of driving the ultrasonic apparatus according to the third embodiment.

FIG. 11 is a flowchart showing the method of driving the ultrasonic apparatus LA according to the present embodiment.

FIGS. 12A through 12D are timing charts of a switching cycle of the switching power supply 263, a frame timing signal, a transmission timing signal of an ultrasonic wave, and a reception timing signal of the ultrasonic wave.

In the ultrasonic measurement process of the ultrasonic apparatus 1A, when the operation signal instructing to start the ultrasonic measurement from, for example, an operation unit not shown, the transmission/reception controller 31 of the control section 3A outputs (step S21) the clock signal to the switching power supply 263 using the clock controller 32. Thus, as shown in FIG. 12A, the switching power supply 263 is driven with the switching cycle T.

Then, the timing output unit 311 of the transmission/reception controller 31A outputs (step S22) the frame timing signal. Specifically, as shown in FIG. 12B, the timing output unit 311 outputs the first frame timing signal in sync with the switching cycle. Further, the timing output unit 311 outputs the second frame timing signal at a timing delayed as much as a half cycle to of the switching noise from the switching cycle after a predetermined period related to the first frame signal acquisition process has elapsed from the output timing of the first frame timing signal. Thereafter, the timing output unit 311 continues to output the first frame timing signal and the second frame timing signal.

Further, the transmission/reception controller 31A determines (step S23) whether or not the first frame timing signal has been output.

In the case in which No has been determined in the step S23, the process returns to the step S23 to continue the detection of the first frame timing signal.

In the case in which Yes has been determined in the step S23 (the timing t21 in FIGS. 12A through 12D), the first frame signal acquisition process is started.

In the first frame signal acquisition process, the transmission command unit 312 outputs the transmission command signal in sync with the switching cycle (in sync with the rising edge of the switching cycle). Specifically, the selection circuit 22 connects the drive connection terminals and the transmission circuit 25 to each other, and the transmission process is performed (step S24). Further, as shown in FIG. 12C, the transmission command unit 312 outputs the transmission timing signal at the same time as the transmission command signal. The output period of the transmission timing signal is the time until the transmission of the ultrasonic wave from the ultrasonic probe 2A toward the predetermined direction is completed, and the ultrasonic wave corresponding to one through three pulses is output from each of the ultrasonic element groups 45A, for example.

Then, as shown in FIG. 12D, the reception command unit 313 outputs the reception command signal to the ultrasonic probe 2A in sync with the falling edge timing t22 of the transmission timing signal. Specifically, the selection circuit 22 connects the drive connection terminals and the reception circuit 233 to each other, and the reception process is performed (step S25). Further, as shown in FIG. 12D, the reception command unit 313 outputs the reception timing signal at the same time as the reception command signal. The output period of the reception timing signal is a period in which the reflected ultrasonic wave from the target area can be received by the ultrasonic probe 2A. Due to the step S25, the reflected ultrasonic wave at each depth in the transmission direction of the ultrasonic wave is detected, and the first echo signal is output from the reception circuit 233 to the phasing addition circuit 24. Thus, the first addition signal is output from the phasing addition circuit 24 to the control section 3A, and then the first addition signal is stored in the memory 34.

Subsequently, the transmission/reception controller 31A determines (step S26) whether or not the ultrasonic scan of the target area has been completed. It should be noted that in the step S26, it is possible to determine whether or not the transmission/reception process (the step S24 and the step S25) of the ultrasonic wave with respect to all of the directions set to the target area has been completed, or it is also possible to determine whether or not the time set in advance to the first frame signal acquisition process has elapsed.

In the case in which No has been determined in the step S26, the process returns to the step S24 to continue the transmission/reception process of the ultrasonic wave synchronized with the switching cycle as indicated by the timings t23, t24 shown in FIGS. 12A through 12D.

On the other hand, in the case in which Yes has been determined in the step S26, the transmission/reception controller 31A determines (step S27) whether or not the second frame timing signal has been output by the timing output unit 311.

In the case in which No has been determined in the step S27, the process returns to the step S27 to continue to detect the output of the second frame timing signal.

In the case in which Yes has been determined in the step S27 (the timing t25 in FIGS. 12A through 12D), the second frame signal acquisition process is started.

In the second frame signal acquisition process, the transmission command unit 312 outputs the transmission command signal at the timing t25 delayed as much as a half cycle to of the switching noise with respect to the switching cycle. In other words, the transmission process is performed (step S28). Further, similarly to the first frame signal acquisition process, the transmission command unit 312 outputs the transmission timing signal at the same time as the transmission command signal.

Then, as shown in FIG. 12D, the reception command unit 313 outputs the reception command signal to the ultrasonic probe 2A in sync with the falling edge timing t26 of the transmission timing signal. In other words, the reception process is performed (step S29). Further, similarly to the first frame signal acquisition process, the reception command unit 313 outputs the reception timing signal at the same time as the reception command signal. Due to the step S29, the reflected ultrasonic wave at each depth in the transmission direction of the ultrasonic wave is detected, and the second echo signal is output from the reception circuit 233 to the phasing addition circuit 24. Thus, the second addition signal is output from the phasing addition circuit 24 to the control section 3A, and then the second addition signal is stored in the memory 34.

Subsequently, the transmission/reception controller 31A determines (step S30) whether or not the ultrasonic scan of the target area has been completed. It should be noted that in the step S30, similarly to the step S26, it is possible to determine whether or not the transmission/reception process (the step S28 and the step S29) of the ultrasonic wave with respect to all of the directions set to the target area has been completed, or it is also possible to determine whether or not the time set in advance to the second frame signal acquisition process has elapsed.

In the case in which No has been determined in the step S30, the process returns to the step S28 to continue the transmission/reception process of the ultrasonic wave synchronized with the switching cycle as indicated by the timings t27, t28 shown in FIGS. 12A through 12D.

On the other hand, in the case in which Yes has been determined in the step S30, the image processor 33A reads out (step S31) each of the first addition signal and the second addition signal stored in the memory 34.

Then, the image processor 33A adds the signals, which have the same ultrasonic reflection direction (the transmission direction) out of the first addition signals and the second addition signals, to each other to generate (step S32) the addition processed signal. Here, the first addition signal and the second addition signal are each a signal on which the switching noise is superimposed, and which has the switching noise components superimposed on each other due to the phasing addition process. However, since the switching noise component in the first addition signal and the switching noise component in the second addition signal exist at respective positions shifted as much as a half cycle to from each other, by performing the addition process on the first addition signal and the second addition signal as described above, the switching noise components are cancelled out with each other to be attenuated.

Subsequently, the image processor 33A generates the internal tomographic image of the object based on the addition processed signal calculated in the step S31, and then makes the display section 4 display (step S33) the result.

Further, the control section 3A determines (step S34) whether or not the measurement of the internal tomographic image with the ultrasonic wave is continued. In the case in which Yes has been determined in the step S34, the process returns to the step S23.

Functions and Advantages of Present Embodiment

In the ultrasonic apparatus 1A according to the present embodiment, the ultrasonic probe 2A is provided with the ultrasonic device 21, the transmission circuit 25 for performing the transmission process of the ultrasonic wave using the ultrasonic device 21, and the reception circuit 233 for processing the reception signal from each of the ultrasonic element groups 45A of the ultrasonic device 21 to output the echo signal. The reception circuit 233 is driven by the electrical power from the switching power supply 263 driven with the predetermined switching cycle T.

Further, the transmission/reception controller 31A of the control section 3A performs the transmission/reception process of the ultrasonic wave in sync with the switching cycle. On this occasion, the phasing addition circuit 24 performs the phasing addition process on the first echo signals output from the reception circuit 233, and then the result is stored in the memory 34 as the first addition signal. Further, the transmission/reception controller 31A of the control section 3A performs the transmission/reception process of the ultrasonic wave at the timing delayed as much as a half cycle of the switching noise with respect to the switching cycle. On this occasion, the phasing addition circuit 24 performs the phasing addition process on the second echo signals output from the reception circuit 233, and then the result is output to the control section 3A as the second addition signal. Then, the image processor 33A performs the addition process on the first addition signal and the second addition signal stored in the memory 34, and then outputs the result as the addition processed signal.

In the ultrasonic apparatus 1A having such a configuration, the switching noise to be superimposed on the first addition signal (the first echo signals) and the switching noise to be superimposed on the second addition signal (the second echo signals) appear so as to be shifted as much as a half cycle to of the switching noise from each other. Therefore, if the first addition signal and the second addition signal are added to each other, the switching noises are cancelled out with each other, and as a result, the switching noises are reduced. Therefore, similarly to the first embodiment, the ultrasonic measurement result high in accuracy can be obtained, and the internal tomographic image high in accuracy with respect to the object can be generated.

Further, due to the single reception circuit 233 and the single switching power supply 263, the switching noise can effectively be reduced, and thus, simplification of the configuration can be achieved compared to the first embodiment. Further, with respect to an ultrasonic apparatus equipped with the related art reception circuit and the switching power supply, or with respect to the above, only by incorporating the transmission/reception controller 31A, the clock controller 32, and the image processor 33A, reduction of the switching noise can easily be achieved. The transmission/reception controller 31A, the clock controller 32, and the image processor 33A described above can be configured by, for example, the arithmetic circuit such as the CPU reading and then executing the program stored in the storage such as the memory 34. Therefore, it becomes possible to easily realize the constituents by, for example, installing application software having these functions to an existing ultrasonic probe 2.

MODIFIED EXAMPLES

It should be noted that the invention is not limited to each of the embodiments described above, but includes modifications and improvements within a range where the advantages of the invention can be achieved, and configurations, which can be obtained by, for example, arbitrarily combining the embodiments.

For example, in the third embodiment described above, the first addition signal is defined as the first processed signal according to the invention, the second addition signal is defined as the second processed signal according to the invention, and the image processor 33A is defined as the signal addition section according to the invention, and the configuration of adding the first addition signal and the second addition signal to each other is adopted. In contrast, in the ultrasonic probe 2, it is also possible to adopt a configuration in which, for example, there is provided a memory for storing the first echo signal and the second echo signal, and the phasing addition circuit performs the phasing addition process on the first echo signal and the second echo signal, and then outputs the result to the control section 3A. In this case, the first echo signal becomes the first processed signal according to the invention, the second echo signal becomes the second processed signal according to the invention, and the phasing addition circuit 24 becomes the signal addition section according to the invention. Even in such a case, the switching noise to be superimposed on the first echo signal and the switching noise to be superimposed on the second echo signal are shifted as much as a half cycle to of the switching noise from each other. Therefore, by performing the addition process on these signals, the switching noise can effectively be reduced.

In the first embodiment described above, the clock controller 32 of the control section 3 outputs the clock signal to the first switching power supply 261 and the second switching power supply 262 to thereby provide the delay corresponding to a half cycle of the switching noise between the drive cycles of the first switching power supply 261 and the second switching power supply 262. In contrast, as described above, it is also possible to output the clock signal from the first switching power supply 261 to the second switching power supply 262, and then make the second switching power supply 262 be driven with a delay corresponding to a half cycle of the switching noise with respect to the clock cycle of the clock signal thus input.

Although in the third embodiment, there is described the example of outputting the clock signal from the clock controller 32 to the switching power supply 263, it is also possible to use, for example, a switching power supply incorporating a related art clock. In this case, the clock signal is output from the switching power supply to the control section 3A. Thus, it becomes possible for the transmission/reception controller 31A to obtain the first addition signal and the second addition signal based on the clock signal (the switching cycle) of the clock signal thus input.

Although in the third embodiment, there is shown the example of performing the first frame signal acquisition process and the second frame signal acquisition process, and then performing the addition process on the first addition signal and the second addition signal, the invention is not limited to this example.

For example, it is also possible to perform the first frame signal acquisition process synchronized with the switching frequency, the second frame signal acquisition process delayed as much as a half cycle of the switching noise with respect to the switching frequency, a third frame signal acquisition process synchronized with the switching frequency, and a fourth frame signal acquisition process delayed as much as a half cycle of the switching noise with respect to the switching frequency. In this case, the addition process is performed on the first addition signal obtained in the first frame signal acquisition process, the second addition signal obtained in the second frame signal acquisition process, the third addition signal obtained in the third frame signal acquisition process, and the fourth addition signal obtained in the fourth frame signal acquisition process, to thereby generate the addition processed signal.

Although in each of the embodiments described above, there is illustrated the configuration of providing the ultrasonic device 21 having a thin film piezoelectric elements 413 stacked on the vibrating film 412, and outputting the ultrasonic wave as the ultrasonic device 21, the invention is not limited to this configuration. As the ultrasonic device, it is also possible to adopt a configuration of arranging, for example, bulk piezoelectric bodies in the scanning direction to perform transmission and reception of the ultrasonic wave. Besides the above, as the configuration of the ultrasonic device 21, any configuration can be illustrated, and it is also possible to adopt, for example, an ultrasonic element of vibrating the vibrating film by applying an alternating-current voltage between the pair of electrodes opposed to each other with a gap.

Further, although there is illustrated the one-dimensional array structure having the ultrasonic element groups 45A arranged along the scanning direction, it is also possible to adopt a configuration of a two-dimensional array structure in which the ultrasonic elements 45 can be driven independently of each other.

Besides the above, specific structures to be adopted when implementing the invention can be configured by arbitrarily combining the embodiments and the modified examples described above with each other, or can arbitrarily be replaced with other structures and so on within the range in which the advantages of the invention can be achieved.

The entire disclosure of Japanese Patent Application No. 2015-177319 filed on Sep. 9, 2015 is expressly incorporated by reference herein.

What is claimed is:

1. An ultrasonic module comprising:
a reception circuit adapted to receive a signal from an ultrasonic probe, which receives an ultrasonic wave, to generate a processed signal;
a switching power supply driven with a predetermined switching cycle, and adapted to supply the reception circuit with electrical power; and
a processor that functions as a signal addition section adapted to perform an addition process on a first processed signal output when driving the reception circuit at a first drive timing in the switching cycle, and a second processed signal output when driving the reception circuit at a second drive timing delayed half cycle of a switching noise in the switching power supply from the first drive timing.

2. The ultrasonic module according to claim 1, wherein the second drive timing is a timing delayed a half cycle with respect to a cycle of a switching $N^{th}$-order harmonic wave of the switching power supply.

3. The ultrasonic module according to claim 1, wherein the ultrasonic probe includes a first ultrasonic reception section, and a second ultrasonic reception section different from the first ultrasonic reception section,
the reception circuit includes a first reception circuit adapted to receive a signal from the first ultrasonic reception section and output the first processed signal, and a second reception circuit adapted to receive a signal from the second ultrasonic reception section and output the second processed signal, and
the switching power supply includes a first switching power supply adapted to supply the first reception circuit with electrical power with the switching cycle from the first drive timing, and a second switching power supply adapted to supply the second reception circuit with electrical power with the switching cycle from the second drive timing.

4. The ultrasonic module according to claim 3, wherein the ultrasonic probe, includes a plurality of ultrasonic element groups arranged along one direction,
the first ultrasonic reception section is constituted by the ultrasonic element groups located at odd-numbered positions along the one direction, and
the second ultrasonic reception section is constituted by the ultrasonic element groups located at even-numbered positions along the one direction.

5. The ultrasonic module according to claim 3, wherein the ultrasonic probe includes a plurality of ultrasonic element groups arranged along one direction,
the first ultrasonic reception section is constituted by the ultrasonic element groups disposed on one side of a central position in the one direction out of the plurality of ultrasonic element groups along the one direction, and
the second ultrasonic reception section is constituted by the ultrasonic element groups disposed on the other side of a central position in the one direction out of the plurality of ultrasonic element groups along the one direction.

6. The ultrasonic module according to claim 3, wherein the processor also functions as a clock control section adapted to control drive timings of the first switching power supply and the second switching power supply.

7. The ultrasonic module according to claim 1, wherein the processor also functions as an ultrasonic control section adapted to perform a transmission process and a reception process of an ultrasonic wave by the ultrasonic probe in sync with each other,
the ultrasonic probe transmits the ultrasonic wave, and
the ultrasonic control section makes the ultrasonic probe perform the transmission process and the reception process in sync with each other at the first drive timing to make the reception circuit output the first processed signal, and makes the ultrasonic probe perform the transmission process and the reception process in sync with each other at the second drive timing to make the reception circuit output the second processed signal.

8. An ultrasonic apparatus comprising:
a reception circuit adapted to receive a signal from an ultrasonic probe, which receives an ultrasonic wave, to generate a processed signal;
a switching power supply driven with a predetermined switching cycle, and adapted to supply the reception circuit with electrical power; and
a processor that functions as
a signal addition section adapted to perform an addition process on a first processed signal output when driving the reception circuit at a first drive timing in the switching cycle, and a second processed signal output when driving the reception circuit at a second drive timing delayed a half cycle of a switching noise in the switching power supply from the first drive timing
a signal addition section adapted to perform an addition process on a first processed signal output when driving the reception circuit at a first drive timing, and a second processed signal output when driving the reception circuit at a second drive timing delayed a half cycle of a switching noise in the switching power supply from the first drive timing; and
an image processing section adapted to generate an internal tomographic image of an object based on a signal obtained by the addition process of the signal addition section.

9. A method of controlling an ultrasonic module including a reception circuit adapted to receive a signal from an ultrasonic probe which receives an ultrasonic wave, to generate a processed signal and a switching power supply driven with a predetermined switching cycle, and adapted to supply the reception circuit with electrical power, the method comprising:
outputting a first processed signal from the reception circuit by driving the reception circuit at a first drive timing in the switching cycle;
outputting a second processed signal from the reception circuit by driving the reception circuit at a second drive timing delayed a half cycle of a switching noise in the switching power supply from the first drive timing; and performing an addition process on the first processed signal and the second processed signal.

* * * * *